United States Patent
Tabata et al.

(10) Patent No.: US 12,371,752 B2
(45) Date of Patent: Jul. 29, 2025

(54) METHOD AND KIT FOR DETECTING INFLUENZA VIRUS, AND METHOD FOR DIAGNOSING INFLUENZA VIRUS INFECTION

(71) Applicant: Japan Science and Technology Agency, Saitama (JP)

(72) Inventors: Kazuhito Tabata, Tokyo (JP); Hiroyuki Noji, Tokyo (JP); Yasuteru Urano, Tokyo (JP); Mako Kamiya, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 957 days.

(21) Appl. No.: 17/435,629

(22) PCT Filed: Mar. 5, 2020

(86) PCT No.: PCT/JP2020/009355
§ 371 (c)(1),
(2) Date: Sep. 1, 2021

(87) PCT Pub. No.: WO2020/179858
PCT Pub. Date: Sep. 10, 2020

(65) Prior Publication Data
US 2022/0145407 A1 May 12, 2022

(30) Foreign Application Priority Data
Mar. 5, 2019 (JP) .............................. JP2019-039299

(51) Int. Cl.
*C12Q 1/70* (2006.01)
*C12Q 1/40* (2006.01)
*G01N 21/64* (2006.01)

(52) U.S. Cl.
CPC .................. *C12Q 1/70* (2013.01); *C12Q 1/40* (2013.01); *G01N 21/6428* (2013.01)

(58) Field of Classification Search
None
See application file for complete search history.

(56) References Cited

U.S. PATENT DOCUMENTS

| | | | |
|---|---|---|---|
| 5,663,055 | A | 9/1997 | Turner et al. |
| 5,719,020 | A | 2/1998 | Liav et al. |
| 6,667,161 | B1 | 12/2003 | Johnson et al. |
| 2004/0086849 | A1 | 5/2004 | Shimasaki et al. |
| 2006/0189775 | A1 | 8/2006 | Takahashi et al. |
| 2009/0220941 | A1 | 9/2009 | Arad et al. |
| 2011/0189655 | A1 | 8/2011 | Li et al. |
| 2012/0147090 | A1 | 6/2012 | Sato et al. |
| 2019/0194717 | A1 | 6/2019 | Noji et al. |

FOREIGN PATENT DOCUMENTS

| | | |
|---|---|---|
| CN | 1285003 A | 2/2001 |
| JP | 2000-501748 A | 2/2000 |
| JP | 2002-541858 A | 12/2002 |
| JP | 2003-511385 A | 3/2003 |
| JP | 2008-275511 A | 11/2008 |
| JP | 2009-516502 A | 4/2009 |
| JP | 2011-139656 A | 7/2011 |
| JP | 2012-121310 A | 6/2012 |
| JP | 2016-006208 A | 1/2016 |
| JP | 2018-038384 A | 3/2018 |
| WO | 9931280 A1 | 6/1999 |
| WO | 2018-043733 A1 | 3/2018 |

OTHER PUBLICATIONS

Yang, W., Liu, X., Peng, X., Li, P., Wang, T., Tai, G., . . . & Zhou, Y. (2012). Synthesis of novel N-acetylneuraminic acid derivatives as substrates for rapid detection of influenza virus neuraminidase. Carbohydrate research, 359, 92-96. (Year: 2012).*
International Search Report and Written Opinion dated May 26, 2020 from PCT International Appln. No. PCT/JP2020/009355 in Japanese, with English language translation of International Search Report.
Miura et al., "Discovery of Human Golgi β-Galactosidase With No Identified Glycosidase Using A QMC Substrate Design Platform for exo-Glycosidase," Bioorganic & Medicinal Chemistry, vol. 24, Feb. 8, 2016, pp. 1369-1375.
Obayashi et al., "A Single-Molecule Digital Enzyme Assay Using Alkaline Phosphatase With A Cumarin-Based Fluorogenic Substrate," Analyst, vol. 140, 2015, pp. 5065-5073.
Rivas et al., "A Novel Sialidase-Activatable Fluorescence Probe With Improved Stability for the Sensitive Detection of Sialidase," Bioorganic & Medicinal Chemistry Letters, vol. 30, No. 126860, published online Dec. 4, 2019, 4 pages.
Liu et al., "Fluorescent Sialic Derivatives for the Specific Detection of Influenza Viruses," Bioorganic & Medicinal Chemistry Letters, vol. 29, No. 126773, Oct. 31, 2019, 5 pages.
Extended European Search Report dated Dec. 23, 2022 issued in European Patent Application No. 20767253.6.
Chinese Office Action dated Nov. 24, 2023, issued in Chinese Patent Application No. 202080018816.0.

* cited by examiner

*Primary Examiner* — Dale R Miller
(74) *Attorney, Agent, or Firm* — Amster, Rothstein & Ebenstein LLP

(57) ABSTRACT

As a technique for detecting an influenza virus with an improved accuracy, there is provided a method for detecting an influenza virus in a biological sample by using a first probe, which is decomposed by an influenza virus-derived neuraminidase and a bacterium-derived neuraminidase to generate an optically detectable signal, and a second probe, which is decomposed by the bacterium-derived neuraminidase to generate an optically detectable signal and not decomposed by the influenza virus-derived neuraminidase.

7 Claims, 8 Drawing Sheets

A

B

C

D

FIG. 3-1
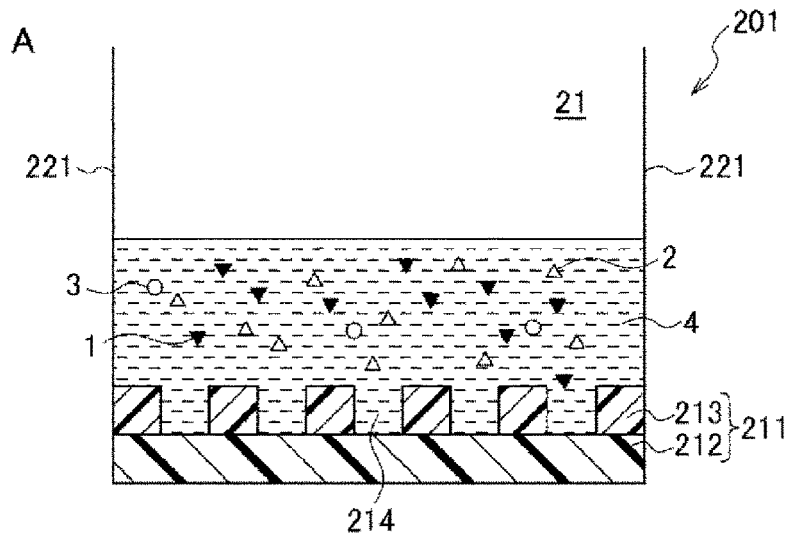
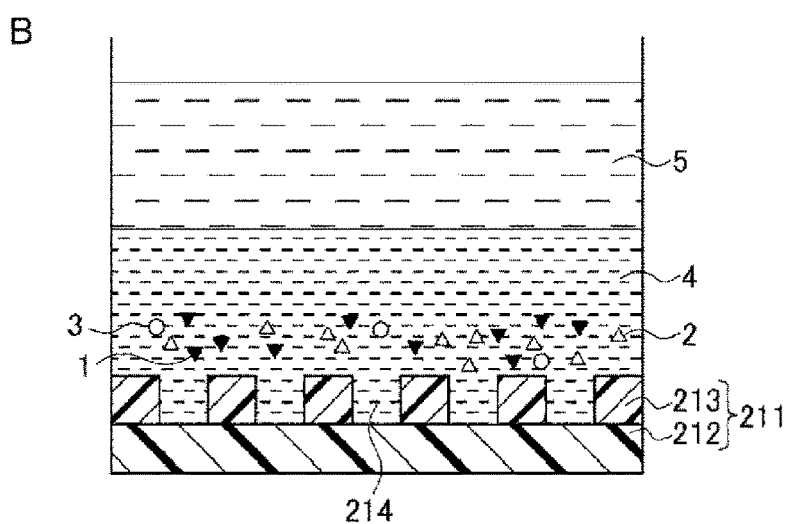
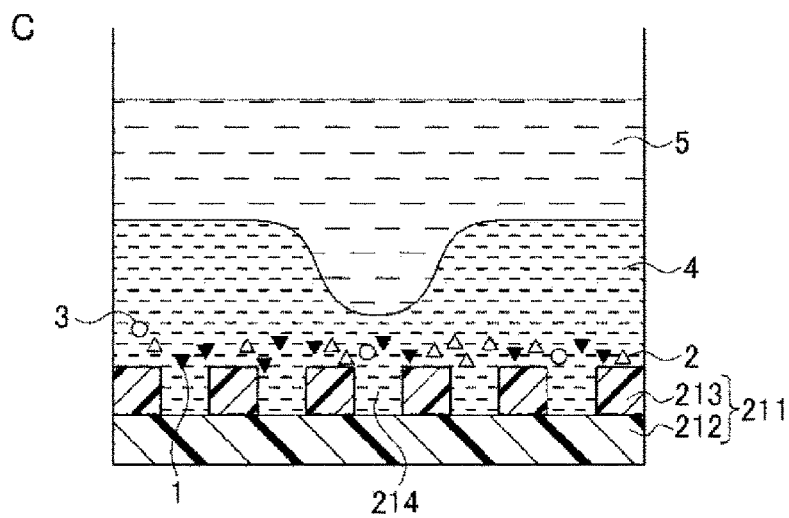

FIG. 3-2
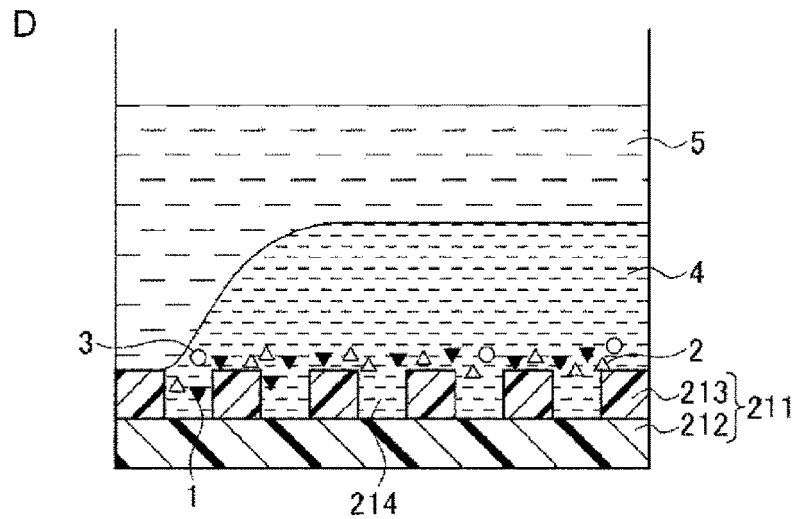
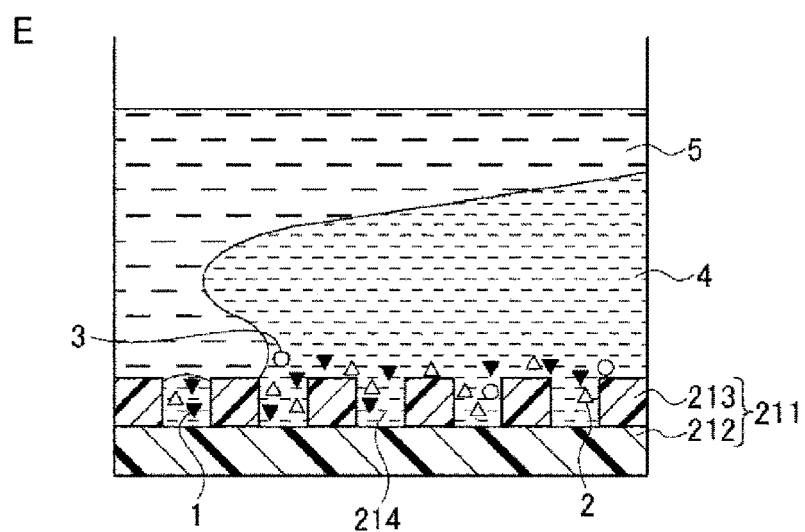
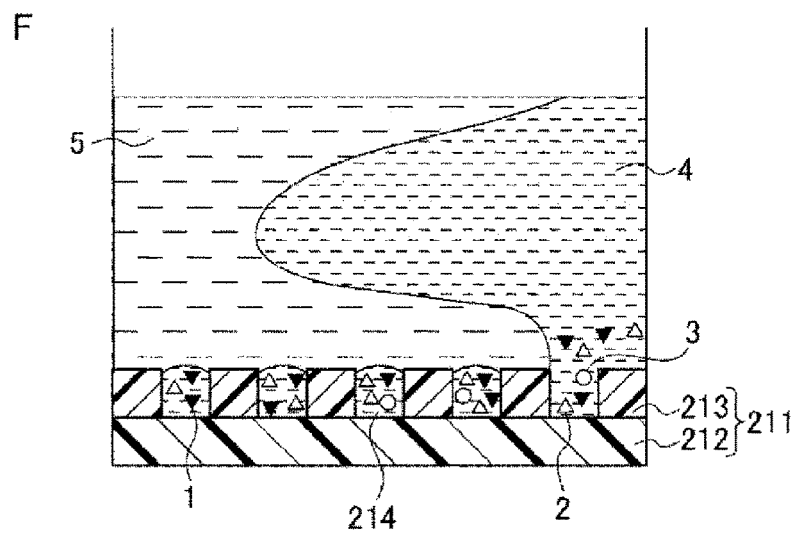

METHOD AND KIT FOR DETECTING INFLUENZA VIRUS, AND METHOD FOR DIAGNOSING INFLUENZA VIRUS INFECTION

CROSS-REFERENCE TO RELATED APPLICATIONS

This application is a U.S. national stage entry under 35 U.S.C. § 371 of PCT International Patent Application No. PCT/JP2020/009355, filed Mar. 5, 2020, which claims priority to Japanese Patent Application No. 2019-039299, filed Mar. 5, 2019, the contents of each of which are hereby incorporated by reference in their entirety.

TECHNICAL FIELD

The present invention relates to a method and kit for detecting an influenza virus and a method for diagnosing influenza virus infection. More specifically, the present invention relates to, e.g., a method for detecting an influenza virus using a substrate reacting to an influenza virus-derived neuraminidase differently from a bacterium-derived neuraminidase.

BACKGROUND ART

Recently, a simple influenza virus test kit using immunochromatography has been developed (see, Patent Literature 1). The method using immunochromatography can detect an influenza virus within several to several tens of minutes. Thus, the method is utilized for, e.g., diagnosing and treating influenza.

Also, a technique for optically detecting an influenza virus based on the reaction between a neuraminidase (Sialidase) that an influenza virus has and a chromogenic substrate, has been known in the technical field (see, Patent Literatures 2, 3). A neuraminidase is an exo-type glycolytic enzyme, which release sialic acid from a non-reducing end of a sugar chain. A neuraminidase is present on the surface of an influenza virus and involved in viral proliferation. As the chromogenic substrate, a chemiluminescent derivative, such as 4-methylumbelliferyl-N-acetyl-α-D-neuraminic acid (4MU-NANA, see Patent Literature 2), 4-alkoxy-N-acetylneuraminic acid or 4,7-dialkoxy-N-acetylneuraminic acid (see Patent Literature 3), is used. For example, in a method using 4MU-NANA as a chromogenic substrate, 4MU-NANA is decomposed by a neuraminidase to generate a fluorescent substance, 4-methylumbelliferone. The value of enzymatic activity of the neuraminidase can be calculated based on the fluorescence intensity of the 4-methylumbelliferone generated. Further based on the value of the enzymatic activity, the number of influenza virus particles can be determined.

Patent Literature 4 discloses a kit for detecting whether influenza of a person is human influenza or human pathogenic avian influenza (see, Example 7). The kit contains a substrate containing N-glycolylneuraminic acid (NeuGcα2-3Gal) bound to galactose and a substrate containing N-acetylneuraminic acid (NeuAcα2-3Gal) bound to galactose. When a clinical specimen is brought into contact with these two types of substrates, if the substrate based on NeuAcα 2-3Gal alone is cleaved, it is determined that the specimen is positive to a human influenza virus, and if the substrate based on NeuAcα 2-3Gal and the substrate based on NeuGcα 2-3Gal are both cleaved, it is determined that the specimen is positive to a human pathogenic avian influenza virus.

Patent Literatures 5 discloses a method for detecting an influenza virus by a digital system. In the digital system, an analyte is introduced into a number of micro-spaces (for example, microdroplets) in a ratio at most one molecule per micro-space. Then, the analyte in each micro-space is subjected to detection, the presence of the analyte is indicated by a numeral value 0 or 1. Owing to the digital system, an analyte can be highly sensitively and quantitatively detected. Patent Literatures 6 and 7 disclose a method/technique for enclosing a substance in micro-spaces applicable to the digital system.

CITATION LIST

Patent Literatures

Patent Literature 1: Japanese Patent Laid-Open No. 2008-275511
Patent Literature 2: Japanese Patent Laid-Open No. 2011-139656
Patent Literature 3: Japanese Translation of PCT International Application Publication No. 2002-541858
Patent Literature 4: Japanese Translation of PCT International Application Publication No. 2009-516502
Patent Literature 5: Japanese Patent Laid-Open No. 2018-038384
Patent Literature 6: Republished Japanese Translation of PCT International Application Publication No. 2012-121310
Patent Literature 7: Republished Japanese Translation of PCT International Application Publication No. 2016-006208

SUMMARY OF INVENTION

Technical Problem

There is a bacterium having a neuraminidase in the indigenous bacteria on the upper respiratory mucous membrane. Because of this, a method for detecting an influenza virus in a specimen such as nasal swab, based on the reaction between a neuraminidase and a substrate thereof has a risk of detecting a signal generated from a bacterium-derived neuraminidase, as a false positive.

In the circumstance, a main object of the present invention is to provide a technique for detecting an influenza virus using a substrate reacting to an influenza virus-derived neuraminidase differently from a bacterium-derived neuraminidase, with an improved accuracy.

Solution to Problem

To attain the above object, the present invention provides the following [1] to [18].

[1] A method for detecting an influenza virus or influenza virus-derived neuraminidase in a biological sample, comprising (1) step 1 of mixing the biological sample with a first probe and a second probe, wherein the first probe is decomposed by an influenza virus-derived neuraminidase and a bacterium-derived neuraminidase to generate an optically detectable signal, the second probe is decomposed by the bacterium-derived neuraminidase to generate an optically detectable signal and not decomposed by the influenza virus-derived neuraminidase, and the signal generated from the first probe and the signal generated from the second probe can be optically discriminatorily detected.

(2) step 2 of detecting signals generated from the first probe and the second probe, wherein (A) if the ratio of an intensity of the signal generated from the first probe to an intensity of the signal generated from the second probe is equal to or more than a predetermined value, the presence of an influenza virus or influenza virus-derived neuraminidase in the biological sample is detected, and if the ratio is less than the predetermined value, the absence of an influenza virus or influenza virus-derived neuraminidase in the biological sample is detected, or (B) if the signal generated from the first probe is detected and the signal generated from the second probe is not detected, the presence of an influenza virus or influenza virus-derived neuraminidase in the biological sample is detected, and if the signal generated from the first probe and the signal generated from the second probe are detected, the absence of an influenza virus or influenza virus-derived neuraminidase in the biological sample, is detected.

[2] The detection method according to [1], wherein the second probe is a compound represented by the following formula (1) or a salt thereof:

[Formula 1]

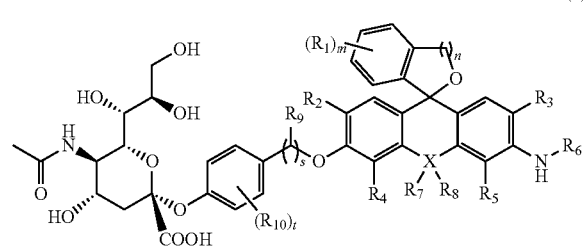

(1)

wherein, $R_1$, if present, represents the same or different monovalent substituents present on a benzene ring, $R_2$ and $R_3$ each independently represent a hydrogen atom, an alkyl group having 1 to 6 carbon atoms or a halogen atom, $R_4$ and $R_5$ each independently represent a hydrogen atom, an alkyl group having 1 to 6 carbon atoms or a halogen atom, $R_6$ represents a hydrogen atom, an alkyl group having 1 to 5 carbon atoms or an alkyl fluoride group having 1 to 5 carbon atoms, $R_7$ and $R_8$, if present, each independently represent an alkyl group having 1 to 6 carbon atoms or an aryl group, wherein if X represents an oxygen atom, neither $R_7$ nor $R_8$ is present, $R_9$ is, independently at each occurrence, selected from a hydrogen atom, an alkyl group having 1 to 5 carbon atoms, an alkoxy group, a hydroxy group, a carboxyl group, a halogen atom, a sulfone group, an amino group, an alkoxycarbonyl group and an oxo group, $R_{10}$, if present, represents the same or different monovalent substituents present on a benzene ring, X represents an oxygen atom, a silicon atom or a carbon atom, m represents an integer of 0 to 4, n represents an integer of 1 to 3, s represents an integer of 1, and t represents an integer of 0 to 4.

[3] The detection method according to [2], wherein $R_6$ in Formula (1) is —$CH_2$—$CF_3$.

[4] The detection method according to any one of [1] to [3], wherein the first probe is 2'-(4-methylumbelliferyl)-α-D-N-acetylneuraminic acid (4MU-NANA).

[5] The detection method according to any one of [1] to [4] wherein if the signal generated from the first probe is detected and the signal generated from the second probe is not detected, the presence of an influenza virus or influenza virus-derived neuraminidase in the biological sample is detected, and if the signal generated from the first probe and the signal generated from the second probe are detected, the absence of an influenza virus or influenza virus-derived neuraminidase in the biological sample is detected.

[6] The detection method according to any one of [1] to [5], based on a digital system.

[7] A kit for detecting an influenza virus or influenza virus-derived neuraminidase in a biological sample isolated from a subject infected or suspected of being infected with an influenza virus, comprising:

a first probe that is decomposed by an influenza virus-derived neuraminidase and a bacterium-derived neuraminidase to generate an optically detectable signal, and a second probe that is decomposed by the bacterium-derived neuraminidase to generate an optically detectable signal and not decomposed by an influenza virus-derived neuraminidase, wherein the second probe is a compound represented by the following formula (1) or a salt thereof:

[Formula 2]

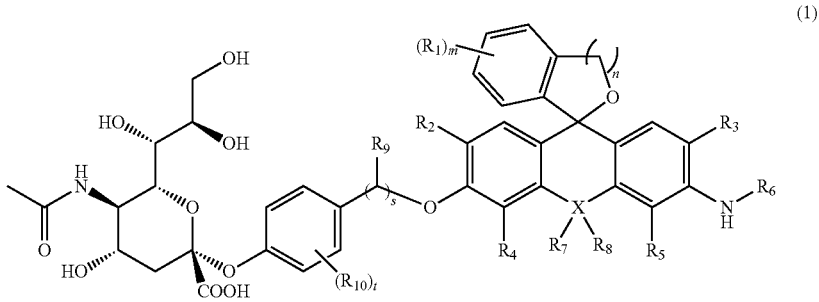

(1)

wherein, $R_1$, if present, represents the same or different monovalent substituents present on a benzene ring, $R_2$ and $R_3$ each independently represent a hydrogen atom, an alkyl group having 1 to 6 carbon atoms or a halogen atom, $R_4$ and $R_5$ each independently represent a hydrogen atom, an alkyl group having 1 to 6 carbon atoms or a halogen atom, $R_6$ represents a hydrogen atom, an alkyl group having 1 to 5 carbon atoms or an alkyl fluoride group having 1 to 5 carbon atoms, $R_7$ and $R_8$, if present, each independently represent an alkyl group having 1 to 6 carbon atoms or an aryl group, wherein if X represents an oxygen atom, neither $R_7$ nor $R_8$ is present, $R_9$ is, independently at each occurrence, selected from a hydrogen atom, an alkyl group having 1 to 5 carbon atoms, an alkoxy group, a hydroxy group, a carboxyl group, a halogen atom, a sulfone group, an amino group, an alkoxycarbonyl group and an oxo group, $R_{10}$, if present, represents the same or different monovalent substituents present on a benzene ring, X represents an oxygen atom, a silicon atom or a carbon atom, m represents an integer of 0 to 4, n represents an integer of 1 to 3, s represents an integer of 1, and t represents an integer of 0 to 4.

[8] The kit according to [7], wherein $R_6$ in Formula (1) is —$CH_2$—$CF_3$.

[9] The kit according to [7] or [8], wherein the first probe is 2'-(4-methylumbelliferyl)-α-D-N-acetylneuraminic acid (4MU-NANA).

[10] Use of a compound represented by the following Formula (1) or a salt thereof for discriminatorily detecting an influenza virus or an influenza virus-derived neuraminidase from a bacterium or a bacterium-derived neuraminidase, wherein $R_1$, if present, represents the same or different monovalent substituents present on a benzene ring, $R_2$ and $R_3$ each independently represent a hydrogen atom, an alkyl group having 1 to 6 carbon atoms or a halogen atom;

$R_4$ and $R_5$ each independently represent a hydrogen atom, an alkyl group having 1 to 6 carbon atoms or a halogen atom, $R_6$ represents a hydrogen atom, an alkyl group having 1 to 5 carbon atoms or an alkyl fluoride group having 1 to 5 carbon atoms, $R_7$ and $R_8$, if present, each independently represent an alkyl group having 1 to 6 carbon atoms or an aryl group, wherein if X represents an oxygen atom, neither $R_7$ nor $R_8$ is present, $R_9$ is, independently at each occurrence, selected from a hydrogen atom, an alkyl group having 1 to 5 carbon atoms, an alkoxy group, a hydroxy group, a carboxyl group, a halogen atom, a sulfone group, an amino group, an alkoxycarbonyl group and an oxo groups, $R_{10}$, if present, represents the same or different monovalent substituents present on a benzene ring, X represents an oxygen atom, a silicon atom or a carbon atom, m represents an integer of 0 to 4, n represents an integer of 1 to 3, s represents an integer of 1, and t represents an integer of 0 to 4.

[11] The use of [10], wherein $R_6$ in Formula (1) is —$CH_2$—$CF_3$.

[12] A reagent for use in discriminatorily detecting an influenza virus or an influenza virus-derived neuraminidase from a bacterium or a bacterium-derived neuraminidase, comprising a compound represented by the following Formula (1) or a salt thereof:

[Formula 3]

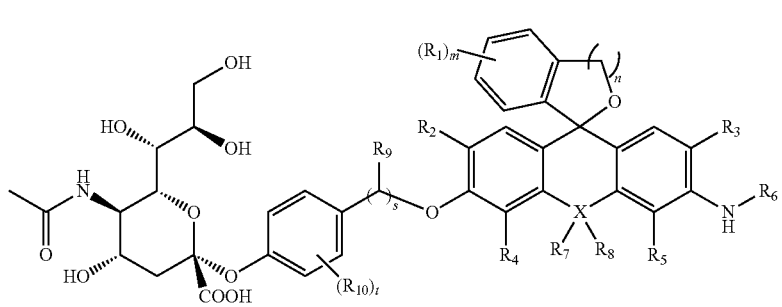

(1)

[Formula 4]

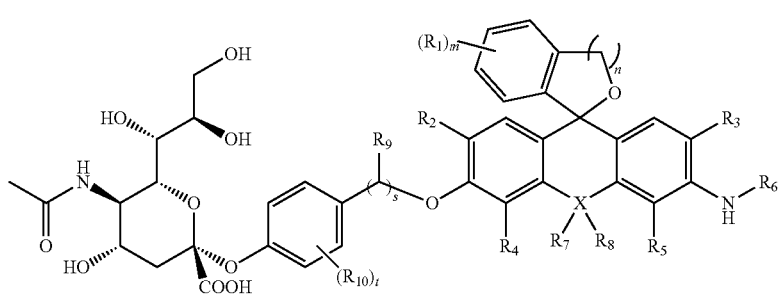

(1)

wherein
$R_1$, if present, represents the same or different monovalent substituents present on a benzene ring,
$R_2$ and $R_3$ each independently represent a hydrogen atom, an alkyl group having 1 to 6 carbon atoms or a halogen atom,
$R_4$ and $R_5$ each independently represent a hydrogen atom, an alkyl group having 1 to 6 carbon atoms or a halogen atom,
$R_6$ represents a hydrogen atom, an alkyl group having 1 to 5 carbon atoms or an alkyl fluoride group having 1 to 5 carbon atoms,
$R_7$ and $R_8$, if present, each independently represent an alkyl group having 1 to 6 carbon atoms or an aryl group, wherein if X represents an oxygen atom, neither $R_7$ nor $R_8$ is present,
$R_9$ is, independently at each occurrence, selected from a hydrogen atom, an alkyl group having 1 to 5 carbon atoms, an alkoxy group, a hydroxy group, a carboxyl group, a halogen atom, a sulfone group, an amino group, an alkoxycarbonyl group and an oxo group,
$R_{10}$, if present, represents the same or different monovalent substituents present on a benzene ring,
X represents an oxygen atom, a silicon atom or a carbon atom,
m represents an integer of 0 to 4,
n represents an integer of 1 to 3,
s represents an integer of 1, and
t represents an integer of 0 to 4.

[13] The reagent according to [12], wherein $R_6$ in Formula (1) is —$CH_2$—$CF_3$.

[14] A method for diagnosing whether a subject is infected or not with an influence virus, comprising:

(1) step 1 of mixing a biological sample, which is isolated from a subject infected or suspected of being infected with an influenza virus, a first probe and a second probe, wherein the first probe is decomposed by an influenza virus-derived neuraminidase and a bacterium-derived neuraminidase to generate an optically detectable signal, the second probe is decomposed by the bacterium-derived neuraminidase to generate an optically detectable signal and not decomposed by the influenza virus-derived neuraminidase, and the signal generated from the first probe and the signal generated from the second probe can be optically discriminatorily detected, (2) step 2 of detecting signals generated from the first probe and the second probe, wherein (A) if the ratio of an intensity of the signal generated from the first probe to an intensity of the signal generated from the second probe is equal to or more than a predetermined value, it is determined that the subject is infected with an influenza virus, and if the ratio is less than the predetermined value, it is determined that the subject is not infected with an influenza virus, or (B) if the signal generated from the first probe is detected and the signal generated from the second probe is not detected, it is determined that the subject is infected with an influenza virus, and if the signal generated from the first probe and the signal generated from the second probe are detected, it is determined that the subject is not infected with an influenza virus.

[15] The diagnostic method according to [14], wherein $R_6$ in Formula (1) is —$CH_2$—$CF_3$.

[16] The diagnostic method according to [14] or [15], wherein the first probe is 2'-(4-methylumbelliferyl)-α-D-N-acetylneuraminic acid (4MU-NANA).

[17] The diagnostic method according to any one of [14] to [16], wherein if the signal generated from the first probe is detected and the signal generated from the second probe is not detected, it is determined that the subject is infected with an influenza virus, and if the signal generated from the first probe and the signal generated from the second probe are detected, it is determined that the subject is not infected with an influenza virus.

[18] The diagnostic method according to any one of [14] to [17] based on a digital system.

In the specification, the alkyl moiety of an "alkyl group" or a substituent (for example, an alkoxy group) containing an alkyl moiety, unless otherwise specified, refers to, a linear, branched, cyclic alkyl group having, for example, 1 to 6 carbon atoms, preferably 1 to 4 carbon atoms, and further preferably 1 to 3 carbon atoms, or an alkyl group formed of a combination of them. More specifically, examples of the alkyl group include a methyl group, an ethyl group, a n-propyl group, an isopropyl group, a cyclopropyl group, a n-butyl group, a sec-butyl group, an isobutyl group, a tert-butyl group, a cyclopropylmethyl group, a n-pentyl group and a n-hexyl group.

In the specification, the "halogen atom" may be any one of a fluorine atom, a chlorine atom, a bromine atom and an iodine atom, and preferably, a fluorine atom, a chlorine atom or a bromine atom.

Advantageous Effects of Invention

The present invention provides a technology for detecting an influenza virus with an improved accuracy.

BRIEF DESCRIPTION OF DRAWINGS

FIG. 3-1 is an illustrative drawing of another embodiment of step 2 in a method for detecting an influenza virus according to the present invention.

FIG. 3-2 is an illustrative drawing of another embodiment of step 2 in a method for detecting an influenza virus according to the present invention.

FIG. 3-3 is an illustrative drawing of another embodiment of step 2 in a method for detecting an influenza virus according to the present invention.

DESCRIPTION OF EMBODIMENTS

Figure 1:
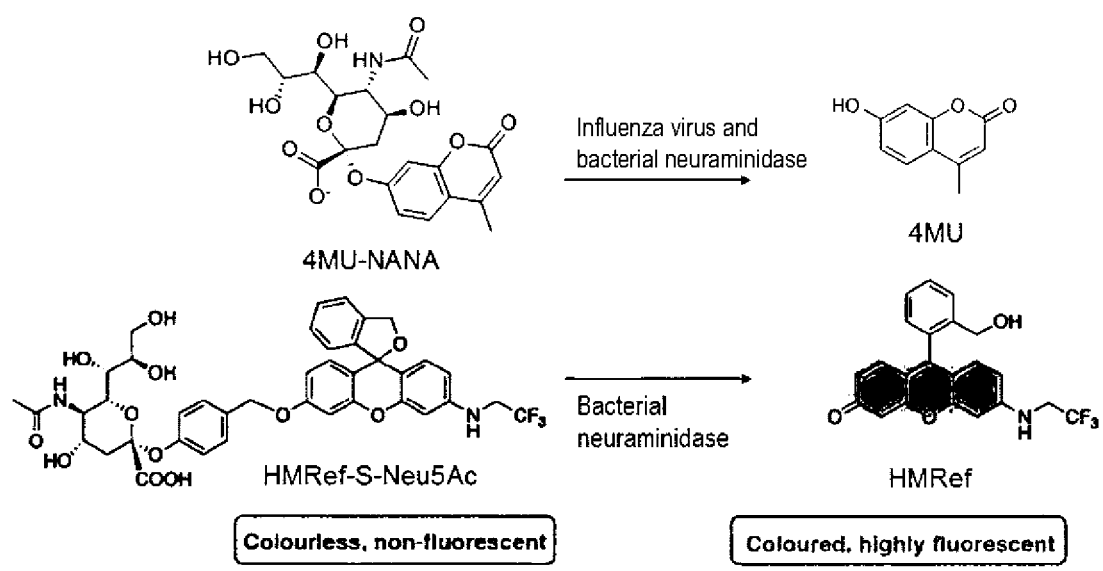
FIG. 1 shows the schemes of the enzymatic hydrolysis reactions of a compound represented by Formula (1), i.e., "HMRef-S-Neu5Ac" and 4MU-NANA with a neuraminidase of an influenza virus or a bacterium.

Now, preferred embodiments for carrying out the present invention will be described with reference to the accompanying drawings. Note that, representative embodiments of the present invention will be described below but these embodiments will not be construed as narrowing the scope of the present invention.

1. Method for Detecting Influenza Virus and Method for Diagnosing Influenza Infection A method for detecting an influenza virus according to the present invention detects an influenza virus based on whether or not a probe is hydrolyzed by an influenza virus-derived neuraminidase. Accordingly, in the present invention, "detection of influenza virus" and "detection of an influenza virus-derived neuraminidase" are interchangeably used.

The method for detecting an influenza virus according to the present invention include the following steps 1 and 2.

Step 1: step of mixing a biological sample with a first probe and a second probe.

Step 2: step of detecting signals generated from the first probe and the second probe.

1-1. Step 1 (Mixing a Biological Sample and Probes)
[Biological Sample]

The biological sample of the present invention is not particularly limited as long as it may contain an influenza virus and is derived from a living body.

Examples of the biological sample include nasal aspirate, nasal swab, pharynx swab, trachea swab, saliva, sputum, blood (including whole blood, serum and plasma), urea, cells, tissue and an extract from an organ.

In the method for diagnosing influenza according to the present invention, a biological sample is isolated from a subject infected or suspected of being infected with an influenza virus.

The subjects are not limited to humans and may be mammals including a monkey and a pig, and birds including a duck and a chicken.

[Probe 1]

A first probe (hereinafter referred to as "probe 1") is hydrolyzed with an influenza virus-derived neuraminidase and a bacterium-derived neuraminidase to generate an optically detectable signal.

In the present invention, the term "bacterium" is used in the broadest sense referring to all prokaryotes including archaea, and particularly refers to eubacteria that can be normally present in biological samples.

Examples of the indigenous bacteria in, e.g., the nasal cavity, laryngopharynx, oral cavity and urinary organ, include bacteria belonging to various genera, such as *Actinomyces, Bacteroides, Clostridium, Corynebacterium, Enterobacteriaceae, Eubacterium, Fusobacterium, Haemophilus, Lactobacillus, Micrococcus, Mycobacterium, Mycoplasma, Neisseria, Peptostreptococcus, Porphyromonas, Prevotella, Propinibacterium, Salmonella, Staphylococcus, Streptococcus*, Spirohaetaceae and *Veillonella*. These bacteria may contain a neuraminidase.

Probe 1 is not limited as long as it is a compound containing sialic acid, the glycosidic bond of which is hydrolyzed by an influenza virus-derived neuraminidase and a bacterium-derived neuraminidase to produce a reaction product different in optical property from the compound before hydrolysis. A change in optical property from probe 1 before hydrolysis to the reaction product obtained after hydrolysis is detected as "an optically detectable signal".

The change in optical property refers to a change in absorbance, optical rotation and refractive index, and a change in fluorescence (emission or non-emission) or a change in fluorescence intensity.

As probe 1, a compound prepared by binding a chromophore to neuraminic acid or a derivative thereof can be suitably used.

The chromophore may be a fluorescent substance or a chemiluminescent substance and preferably a fluorescent substance. Examples of the fluorescent substance include substances known in the technical field, such as 4-methylumbelliferone, fluorescein, resorufin and rhodamine.

As Probe 1, for example, 2'-(4-methylumbelliferyl)-α-D-N-acetylneuraminic acid (4MU-NANA) is frequently used. If 4MU-NANA comes into contact with a neuraminidase derived from an influenza virus or a bacterium and reacts with the neuraminidase, a fluorescent substance, 4-methylumbelliferone, is released.

[Probe 2]

A second probe (hereinafter referred to as "probe 2") is not decomposed by an influenza virus-derived neuraminidase but decomposed only by a bacterium-derived neuraminidase to generate an optically detectable signal.

Probe 2 is not limited as long as it is a compound containing sialic acid, the glycosidic bond of which is not decomposed by an influenza virus-derived neuraminidase but decomposed by a bacterium-derived neuraminidase to produce a reaction product different in optical property from the compound before hydrolysis. A change in optical property from probe 2 before hydrolysis to the reaction product obtained after hydrolysis is detected as "an optically detectable signal".

The "optically detectable signal" generated by probe 2 differs from the "optically detectable signal" generated by probe 1. In other words, the signal generated by probe 2 and the signal generated by probe 1 can be optically discriminatorily detected.

More specifically, if the signal generated by probe 1 is, for example, a change in absorbance, optical rotation and refractive index, the signal generated by probe 2 may be a change in fluorescence (emission or non-emission) or a change in fluorescence intensity. In this case, the signal generated by probe 2 may be a change in absorbance, optical rotation and refractive index in the wavelength range different from that of the signal generated by probe 1.

If the signal generated by probe 1 is a change in fluorescence (emission or non-emission) or a change in fluorescence intensity, the signal generated by probe 2 may be a change in absorbance, optical rotation and refractive index. In this case, the signal generated by probe 2 may be a change in fluorescence (emission or non-emission) or a change in fluorescence intensity in a wavelength range different from the wavelength range of the signal generated by probe 1.

As the probe 2, a compound represented by the following Formula (1) or a salt thereof (hereinafter also referred to simply as "compound (1)") is suitably used.

[Formula 5]

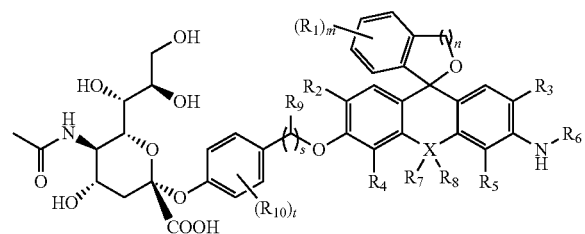

(1)

In Formula (1), $R_1$, if present, represents the same or different monovalent substituents present on a benzene ring. Examples of the monovalent substituent include a halogen atom and an optionally substituted alkyl group.

m represents an integer of 0 to 4.

In a preferred aspect of the present invention, m is 0, that is, $R_1$ is not present, which represents a benzene ring has no substituents.

In Formula (1), $R_2$ and $R_3$ each independently represent a hydrogen atom, an alkyl group having 1 to 6 carbon atoms or a halogen atom.

If $R_2$ and $R_3$ each represent an alkyl group, the alkyl group may have one or two or more substituents such as a halogen atom, a carboxy group, a sulfonyl group, a hydroxy group, an amino group and an alkoxy group. The alkyl group represented by $R_2$ or $R_3$ may be, e.g., a halogenated alkyl group, a hydroxyalkyl group or a carboxyalkyl group. It is preferable that $R_2$ and $R_3$ each independently represent a hydrogen atom or a halogen atom, and more preferable that $R_2$ and $R_3$ simultaneously represent a fluorine atom or a chlorine atom.

$R_4$ and $R_5$ each independently represent a hydrogen atom, an alkyl group having 1 to 6 carbon atoms or a halogen atom, similarly to the case of $R_2$ and $R_3$. It is preferable that $R_4$ and $R_5$ simultaneously represent a hydrogen atom.

$R_6$ represents a hydrogen atom, an alkyl group having 1 to 5 carbon atoms or an alkyl fluoride group having 1 to 5 carbon atoms. As the alkyl group represented by $R_6$, a methyl group or an ethyl group is preferable. As the alkyl fluoride group represented by $R_6$, $-CH_2-CF_3$ or $-CH_2-CH_2-CF_3$ is preferable.

In a preferred aspect of the present invention, $R_6$ is $-CH_2-CF_3$.

In Formula (1), $R_7$ and $R_8$, if present, each independently represent an alkyl group having 1 to 6 carbon atoms or an aryl group. It is preferable that $R_7$ and $R_8$ each independently represent an alkyl group having 1 to 3 carbon atoms, and more preferable that $R_7$ and $R_8$ simultaneously represent a methyl group. The alkyl group represented by each of $R_7$ and $R_8$ may have one or two or more substituents such as a halogen atom, a carboxy group, a sulfonyl group, a hydroxy group, an amino group and an alkoxy group. The alkyl group represented by $R_7$ or $R_8$ may be, e.g., a halogenated alkyl group, a hydroxyalkyl group or a carboxyalkyl group.

If $R_7$ or $R_8$ represents an aryl group, the aryl group may be either a monocyclic aromatic group or a condensed-ring aromatic group. The aryl ring may contain one or two or more heteroatoms (for example, nitrogen atom, oxygen atom or sulfur atom) as ring-component atoms. The aryl group is preferably a phenyl group. One or two or more substituents may present on the aryl ring. Examples of the substituents include a halogen atom, a carboxy group, a sulfonyl group, a hydroxy group, an amino group and an alkoxy group. One or two or more these substituents may be present.

If X described later is an oxygen atom, neither $R_7$ nor $R_8$ is present.

$R_9$ is, independently at each occurrence, selected from a hydrogen atom, an alkyl group having 1 to 5 carbon atoms, an alkoxy group, a hydroxy group, a carboxyl group, a halogen atom, a sulfone group, an amino group, an alkoxycarbonyl group and an oxo group, and preferably, a hydrogen atom.

s represents an integer of 1.

$R_{10}$, if present, represents the same or different monovalent substituents present on a benzene ring.

Examples of the monovalent substituent include a halogen atom and an optionally substituted alkyl group.

t represents an integer of 0 to 4.

In a preferred aspect of the present invention, t is 0, that is, $R_{10}$ is not present, which represents a benzene ring has no substituents.

X represents an oxygen atom, a silicon atom or a carbon atom.

In a preferred aspect of the present invention, X represents an oxygen atom.

n represents an integer of 0 to 3, and preferably, 1.

A compound represented by Formula (1) can be present in the form of an acid addition salt or a base addition salt.

Examples of the acid addition salt include mineral acid salts such as a hydrochloride, a sulfate and a nitrate; and organic acid salts such as a methanesulfonate, a p-toluene sulfonate, an oxalate, a citrate and a tartrate.

Examples of the base addition salt include metal salts such as a sodium salt, a potassium salt, a calcium salt and a magnesium salt; and organic amine salts such as an ammonium salt or a triethylamine salt.

A compound represented by Formula (1) sometimes forms a salt with an amino acid such as glycine.

A compound (1) may be present in the form of a hydrate or a solvate.

A compound (1) sometimes has one or two or more asymmetric carbons depending on the type of substituent. An optically active substance based on one or two or more asymmetric carbons, a stereoisomer such as a diastereoisomer based on two or more asymmetric carbons, any mixture of stereoisomers and a racemic body are included in the scope of the present invention.

A method for producing a representative compound (1) will be specifically described in Examples of the specification. Those skilled in the art can produce a compound (1) by appropriately selecting, e.g., starting materials, the reaction conditions and reagents based on the description of Examples, and modifying or improving the method of the invention, if necessary.

It has been found that a compound (1) is not decomposed by an influenza virus-derived neuraminidase but decomposed only by a bacterium-derived neuraminidase to generate highly intensive fluorescence (see, Experimental Example 1, Experimental Example 2). The scheme of an enzymatic hydrolysis reaction of a compounds (1), "HMRef-S-Neu5Ac" (see, Synthesis Example 1) by a neuraminidase is shown in FIG. 1.

Accordingly, the compound (1) can be used as a fluorescent probe for discriminatorily detecting an influenza virus or an influenza virus-derived neuraminidase from a bacterium or a bacterium-derived neuraminidase.

The present invention provides a reagent containing a compound (1) for use in discriminatorily detecting an influenza virus or an influenza virus-derived neuraminidase from a bacterium or a bacterium-derived neuraminidase. The reagent may be a compound (1) dried or a compound (1) dissolved in an appropriate buffer solution. Note that, as the buffer solution, those described later can be appropriately used.

A mixture of a biological sample, probe 1 and probe 2 may be prepared by mixing respective solutions of the biological sample, probe 1 and probe 2 dissolved in the same or different aqueous solvents or by dissolving a biological sample, probe 1 and probe 2 in a single aqueous solvent.

[Hydrophilic Solvent]

A hydrophilic solvent is not particularly limited as long as the solvent is routinely used as a reaction solution for an enzyme. For example, water or a buffer solution prepared by adding a buffer substance in water at a concentration required for optimization of an enzymatic reaction, is used.

Examples of the buffer substance that can be used include, but are not particularly limited to, so-called good's buffers, such as MES (2-morpholinoethanesulfonic acid), ADA (N-(2-acetamido)iminodiacetic acid), PIPES (piperazine-1,4-bis(2-ethanesulfonic acid)), ACES (N-(2-acetamido)-2-aminoethanesulfonic acid), BES (N,N-bis(2-hydroxyethyl)-2-aminoethanesulfonic acid), TES (N-tris (hydroxymethyl)methyl-2-aminoethanesulfonic acid) and HEPES (4-(2-hydroxyethyl)-1-piperazineethanesulfonic acid), Tris (tris (hydroxymethyl)aminomethane) and DEA (diethanolamine).

A mixture of a biological sample, probe 1 and probe 2 in solution is incubated for an enzymatic reaction, if necessary. Incubation is carried out, for example, at room temperature to 37° C. for several to several tens of minutes.

1-2. Step 2 (Step of Detecting Signal)

Signals generated from probe 1 and probe 2 are detected by use of an apparatus known in the technical field, such as an image sensor, a spectrophotometer, an optical rotation meter, a spectral fluorometer and a fluorescence microscope, and expressed by numerical values. The mixture of a biological sample, probe 1 and probe 2 in a solution (hereinafter also referred to as a "sample solution") is loaded in an apparatus, and then, measurement may be carried out in accordance with the operation manual for the apparatus.

Probe 1 is decomposed by an influenza virus-derived neuraminidase and a bacterium-derived neuraminidase to generate an optically detectable signal. The intensity of the signal generated from probe 1 is defined as S1.

In contrast, probe 2 is hydrolyzed with only by the bacterium-derived neuraminidase to generate an optically detectable signal. The intensity of the signal generated from probe 2 is defined as S2.

If the neuraminidase present in a sample solution is derived from a bacterium (subject is not infected), signals are generated from both of probe 1 and probe 2.

In contrast, if the neuraminidase present in a sample solution is derived from an influenza virus (subject is infected), a signal is generated from probe 1 but the signal generated from probe 2 is theoretically zero or virtually small even in consideration of the signal generated by spontaneous decomposition of probe 2 (decomposition not by the enzymatic activity of neuraminidase).

Accordingly, compared to the ratio (S1/S2) of S1 to S2 in a sample solution containing a bacterium-derived neuraminidase (a subject is not infected), the ratio in a sample solution containing an influenza virus-derived neuraminidase (a subject is infected) is larger.

More specifically, if the ratio (S1/S2) (which is a ratio of an intensity S1 of the signal generated from probe 1 to an intensity S2 of the signal generated from probe 2) is equal to or more than a predetermined value (threshold), it can be determined that an influenza virus is present in a sample solution (a subject is infected with an influenza virus).

In contrast, if the ratio (S1/S2) is less than the threshold, it can be determined that an influenza virus is not present in the sample solution (a subject is not infected with an influenza virus).

As described above, whether a neuraminidase present in a biological sample is derived from an influenza virus or a bacterium can be clearly discriminated, with the result that an influenza virus can be detected with a high accuracy without detecting a signal derived from a bacterium-derived neuraminidase as a false positive.

The threshold can be appropriately set in accordance with the compounds to be used as probe 1 and probe 2, the optical properties of the probes and the types of bacteria that may be present in a biological sample. For example, the threshold can be set at a value 1.1, 1.5, 2, 3, 4, 5, 6, 7, 8, 9, 10, 20, 30, 40 or 50 times or more as large as the ratio (S1/S2) of the case where a bacterium-derived neuraminidase is present in a sample solution.

If spontaneous decomposition of probe 2 does not occur (not decomposed by enzymatic activity of neuraminidase) or is ignorable, and if neuraminidase present in a sample solution is derived from an influenza virus (a subject is infected), the signal generated from probe 2 is zero. In this case, detection of an influenza virus can be made not based on the ratio (S1/S2) (the ratio of an intensity S1 of a signal generated from probe 1 to an intensity S2 of a signal generated from probe 2).

In other words, if the signal generated from probe 1 is detected and the signal generated from probe 2 is not detected, the presence of an influenza virus in a sample solution (a subject is infected with an influenza virus) can be detected, and if signals generated from probe 1 and probe 2 are detected, the absence of an influenza virus in a sample solution (a subject is not infected with an influenza virus) can be detected.

1-2-1. Detection 1 Based on Digital System

An embodiment of a method having step 2 to which a digital system is applied, will be described.

In the digital system, an analyte is introduced into a number of micro-spaces (for example, microdroplets) in such a manner that at most one molecule of the analyte is present. The analyte in individual micro-spaces is detected and the presence is expressed by 0 or 1. In this way, the analyte can be quantitatively detected with a high degree of sensitivity in the digital system.

According to the embodiment, step 2 includes the following steps 2A1 to 2A3.

Step 2A1: step of introducing a sample solution into the space, which is formed between a lower-layer portion, on which a plurality of accommodation sites that can accommodate an influenza virus particle and a bacterial cell are formed with a division wall having a hydrophobic upper surface interposed between them, and the upper-layer portion facing to the surface of the lower-layer portion on which the accommodation sites are formed.

Step 2A2: step of introducing a hydrophobic solvent into the space to form liquid droplets of the sample solution containing an influenza virus and/or bacterial cell and coated with the hydrophobic solvent, within accommodation sites.

Step 2A3: step of detecting signals generated from probe 1 and probe 2 in the droplets.

1-2-1-1. Introduction Step 2A1

Referring to FIG. 2A, introduction step 2A1 will be described.

Array 101 has a flow-cell structure formed by arranging a lower-layer portion 111 and an upper-layer portion 121 so as to face each other with a space 131 interposed between them. The space 131 is used as a fluid-flow channel.

In the lower-layer portion 111, a plurality of accommodation sites 114 that can accommodate influenza virus particles and/or a bacterial cell are formed. The accommodation sites 114 are mutually isolated by a division wall 113 having a hydrophobic upper surface.

The upper-layer portion 121 faces the surface of the lower-layer portion 111 having the accommodation sites 114 formed thereof, with the space 131 interposed between them.

In the step, a sample solution 4 is introduced into the space 131. The sample solution 4 contains probe 1 and probe 2. The sample solution 4 can also contain influenza virus particles or bacterial cells 3. The sample solution 4 can be introduced into the space 131 through a hole (not shown in the figure) formed at least in one of the upper-layer portion 121 and the lower-layer portion 111. The sample solution 4 introduced in the space 131 flows in the space 131 by capillary action. The space 131 is filled with the sample solution in this way.

[Surfactant]

To the sample solution 4, a surfactant may be added. If the surfactant is contained, it is likely that the sample solution 4 is easily introduced into the space 131 and the accommodation sites 114.

Examples of the surfactant include, but are not particularly limited to, TWEEN20 (CAS number: 9005-64-5, polyoxyethylene sorbitan monolaurate) and Triton X-100 (CAS number: 9002-93-1, common name polyethylene glycol mono-4-octylphenyl ether (n≈10)). Although the concentration of a surfactant to be added in the sample solution 4 is not particularly limited, it is preferably 0.01 to 1%.

As the surfactant, a wide variety of surfactants such as an anionic surfactant, a cationic surfactant, a nonionic surfactant, an amphoteric ion surfactant and a natural surfactant can be used.

The anionic surfactants are classified into, e.g., carboxylate, sulfate, sulfonate, and phosphate types. Specific examples thereof include sodium dodecyl sulfate, sodium laurate, α-sulfo fatty acid methyl ester sodium salt, sodium dodecylbenzene sulfonate and sodium dodecyl ethoxylate sulfate. Of them, sodium dodecylbenzene sulfonate is preferably used.

The cationic surfactants are classified into, e.g., quaternary ammonium salt, alkylamine, and heterocyclic amine types. Specific examples thereof include stearyltrimethylammonium chloride, distearyldimethylammonium chloride, didecyldimethylammonium chloride, cetyltripiridinium chloride, and dodecyldimethylbenzylammonium chloride.

Examples of the nonionic surfactants include polyoxyethylene alkyl ether, polyoxyethylene hydrogenated castor oil, polyoxyethylene monofatty acid ester, polyoxyethylene sorbitan monofatty acid ester, sucrose fatty acid ester, polyglycerin fatty acid ester, alkylpolyglycoside, and N-methylalkylglucamide. Of them, not only dodecyl alcohol ethoxylate, nonyl phenol ethoxylate, and lauroyl diethanolamide but also commercially available surfactants under the name of Triton X (e.g., Triton X-100), Pluronic (R) (e.g., Pluronic F-123, F-68), Tween (e.g., Tween 20, 40, 60, 65, 80, 85), Brij (R) (e.g., Brij 35, 58, 98), and Span (e.g., Span 20, 40, 60, 80, 83, 85) are preferred.

Examples of the amphoteric surfactants include lauryldimethylaminoacetic acid betaine, dodecylaminomethyldimethylsulfopropylbetaine, and 3-(tetradecyldimethylaminio) propan-1-sulfonate. Particularly, 3-[(3-colamidpropyl) dimethylammonio]-1-propane sulfonate (CHAPS) and 3-[(3-colamidpropyl)dimethylammonio]-2-hydroxy-1-propane sulfonate (CHAPSO) are preferably used.

As the natural surfactant, lecithin and saponin are preferable. Of the compounds called lecithin, e.g., phosphatidylcholine, phosphatidylethanolamine, phosphatidylinositol, phosphatidylserine, phosphatidic acid and phosphatidylglycerol are preferable. As the saponin, quillaia saponin is preferred.

In the step, probe 1, probe 2 and the influenza virus particles or bacterial cells 3 are introduced into the accommodation sites 114. If an influenza virus particles or bacterial cells are diluted to a sufficiently low concentration in the sample solution 4, the number of influenza viral particles or bacterial cells 3 that can be accommodated in a single accommodation site 114 can be 0 or at most 1. If the concentration of influenza virus particles or bacterial cells in the sample solution 4 is higher, 2 or more virus particles 2 can be introduced in a single accommodation site 114.

1-2-1-2. Enclosure Step 2A2

Referring to FIG. 2B, enclosure step 2A2 will be described. In this step, a hydrophobic solvent 5 is introduced into the space 131 between the lower-layer portion 111 and the upper-layer portion 121.

It is sufficient if the hydrophobic solvent 5 is a solvent (immiscible solvent) less miscible with the sample solution 4. A hydrophobic solvent is preferably used for the sample solution 4 as a hydrophilic solvent.

As the hydrophobic solvent 5, at least one selected from the group consisting of, for example, a saturated hydrocarbon, an unsaturated hydrocarbon, an aromatic hydrocarbon, silicone oil, perfluorocarbon, a halogen based solvent and a hydrophobic ionic liquid, or a mixture containing the at least one of them can be suitably used. Examples of the saturated hydrocarbon include an alkane and a cycloalkane. Examples of the alkane include decan and hexadecane. Examples of the unsaturated hydrocarbon include squalene. Examples of the aromatic hydrocarbon include benzene and toluene. Examples of the perfluorocarbon include Fluorinert (R) FC40 (manufactured by SIGMA). Examples of the halogen solvent include chloroform, methylene chloride and chlorobenzene. The hydrophobic ionic liquid refers to an ionic liquid that does not dissociate at least in water. Examples of the hydrophobic ionic liquid include 1-butyl-3-methylimidazolium hexafluorophosphate. The ionic liquid refers to a salt present as a liquid at room temperature.

The hydrophobic solvent 5 may be introduced into the space 131 through a hole (not shown in the figure) formed at least in one of the upper-layer portion 121 and the lower-layer portion 111, similarly to the sample solution 4. The hydrophobic solvent 5 introduced in the space 131 flows through the space 131 by capillary action and replaces the sample solution 4 in the space 131. The sample solution 4 replaced is discharged from the space 131. In this manner, droplets of the sample solution 4 containing probe 1, probe 2 and an influenza virus particle or bacterial cell 3 and coated with the hydrophobic solvent 5 are formed in the accommodation sites 114.

The volume (substantially equal to the volume of the accommodation sites 114) of the droplets may be extremely small, for example, 10 aL to 100 nL, and preferably 1 fL to 1 pL.

In the droplets of the sample solution 4 extremely small in volume, the reactions of a neuraminidase of an influenza virus or bacterium with probe 1 and probe 2 proceed.

[Deaeration]

The air of the space 131 may be removed between introduction step 2A1 and enclosure step 2A2. For removing air, for example, a method for leaving the array 101 under a reduced-pressure environment or a method of cooling the array 101 can be suitably used. More specifically, a method of placing the array 101 in a vacuum desiccator of about 0.1 atm. for about 30 seconds, may be employed.

In the present invention, the deaeration step is not essential. However, if deaeration is carried out, the air within the accommodation sites 114 is removed and probe 1, probe 2 and the influenza virus particle or bacterial cell 3 can be efficiently introduced in the accommodation sites 114.

1-2-1-3. Detection Step 2A3

In the step, signals from probe 1 and probe 2 generated in the droplets of the sample solution 4 are detected.

As described above, if influenza virus particles or bacterial cells are diluted to a sufficiently low concentration in the sample solution 4, since the number of influenza virus particles or bacterial cells 3 introduced in a single accommodation site 114 becomes 0 or at most 1, a droplet containing either one of an influenza virus particle and a bacterial cell is formed in the accommodation site 114.

In the case where a signal generated from probe 1 is detected and a signal generated from probe 2 is not detected in a droplet (see the left figure of FIG. 2C), an influenza virus can be detected in the droplet. In contrast, in the case where a signal generated from probe 1 and a signal generated from probe 2 are detected (see the right figure of FIG. 2C), the presence of a bacterial cell in the droplet (no influenza virus particle) can be detected.

Figure 2:
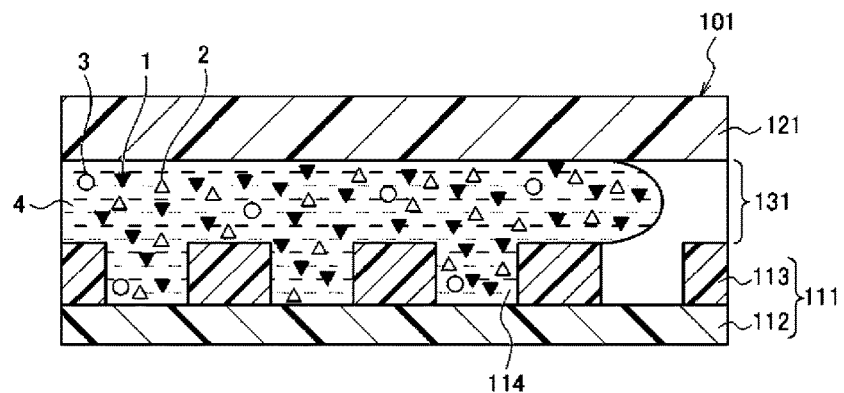
FIG. 2 is an illustrative drawing of an embodiment of step 2 in a method for detecting an influenza virus according to the present invention.
Figure 2:
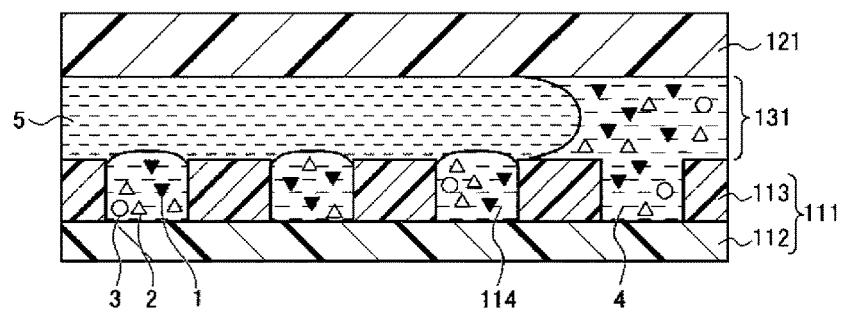
Figure 2:
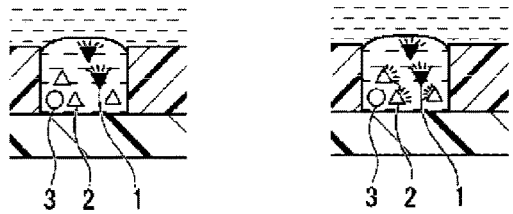
Figure 2:
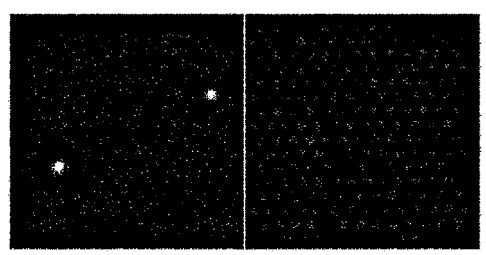

In the digital system where 4MU-NANA is used as probe 1 and HMRef-S-Neu5Ac as a compound (1) is used as probe 2, fluorescence of 4-methylumbelliferone (4MU) generated in droplets containing an influenza virus particle is detected by a CCD camera. An image taken by the camera is shown in FIG. 2D (left figure). Two signal-positive droplets can be observed in a detection area. Blue fluorescence (wavelength 443 nm) emitted by 4MU is detected in droplets containing an influenza virus particle. If a bacterial cell is present in droplets, blue fluorescence (wavelength 443 nm) emitted by 4MU and green fluorescence (wavelength: 518 nm) emitted by HMRef are detected. FIG. 2D (right figure) shows a photographic image of a region where no signal-positive droplets are present.

Using the ratio of the number of the accommodation sites 114 where an influenza virus particle was detected and the number of the accommodation sites 114 where no influenza virus particle was detected and based on a standard curve (previously prepared) defining the relationship between the ratio and the number of virus particles, the amount of an influenza virus can be quantitatively determined (digital quantification).

Note that, even if the number of accommodation sites 114 in which the influenza virus is detected is one, it may be determined that the test sample is positive to influenza. Such a determination method is useful for determining whether or not the patient is affected with influenza in the early stage of infection during which the number of influenza viruses in a sample is extremely small.

1-2-2. Detection 2 Based on Digital System

Another embodiment of a method having a step 2 to which a digital system is applied, will be described.

Step 2 according to the embodiment includes the following steps 2B1 to 2B3.

Step 2B1: step of introducing a sample solution onto a substrate on which a plurality of accommodation sites that can accommodate an influenza virus particle and a bacterial cell are formed with a division wall having a hydrophobic upper surface interposed between them.

Step 2B2: step of introducing a hydrophobic solvent having a larger specific gravity than a sample solution so as to laminate on a layer of the sample solution, and allowing replacement of the sample solution layer and a hydrophobic solvent layer to form liquid droplets of the sample solution containing an influenza virus particle and/or a bacterial cell and coated with the hydrophobic solvent within the accommodation sites.

Step 2B3: step of detecting signals generated from probe 1 and probe 2 in the liquid droplets.

1-2-2-1. Introduction Step 2B1

Figure 3:
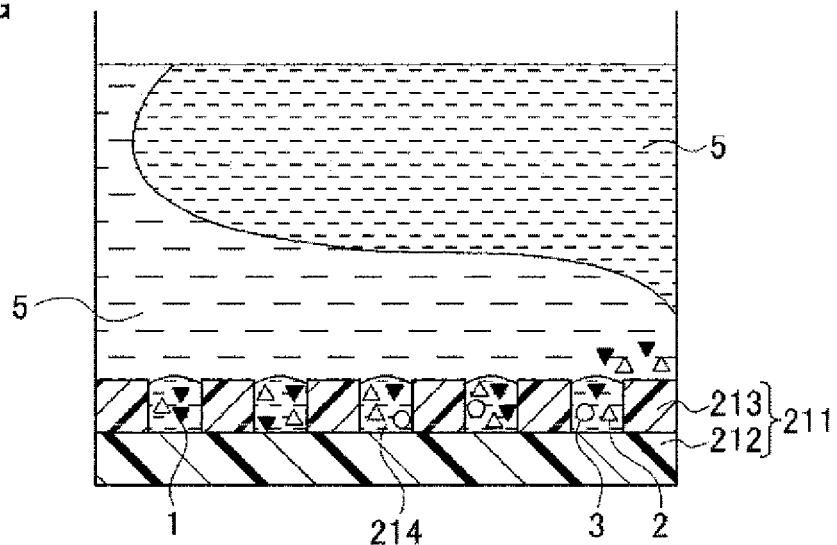
Figure 3:
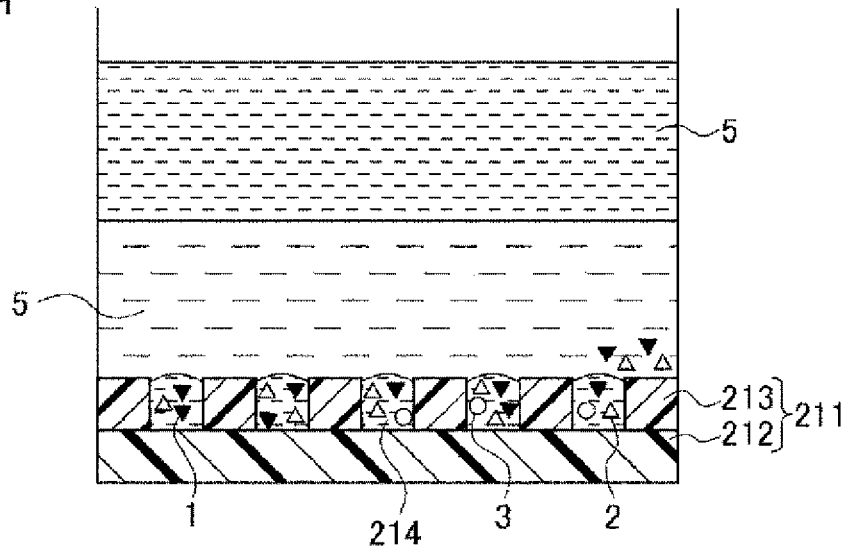

Referring to FIG. 3-1 to FIG. 3-3, introduction step 2B1 will be described. Figures show cross sectional view of an array 201 (as viewed from a side).

The array 201 has a lower-layer portion 211. The array 201 has a region 21, which is separated from the outside by the lower-layer portion 211 on the lower side and by side walls 221, 221 on both sides, and has an opening on the upper side. More specifically, an open well having an above opening is formed of the lower-layer portion 211 and the side walls 221, 221. The space of the open well is defined as the region 21, in the figures.

In the lower-layer portion 211, a plurality of accommodation sites 214 that can accommodate an influenza virus particle and/or a bacterial cell are formed. The accommodation sites 214 are mutually separated by a division wall 213 having a hydrophobic upper surface. The lower-layer portion 211 has no opposite surface to which the portion 211 faces.

In the step, the sample solution 4 is introduced onto the lower-layer portion 211. The sample solution 4 contains probe 1 and probe 2. The sample solution 4 may contain an influenza virus particle or bacterial cell 3. The sample solution can be introduced into the region 21, for example, by the opening of the open well.

To the sample solution 4, a surfactant may be added. If the surfactant is contained, replacement between the sample solution 4 and a hydrophobic solvent in the following enclosure step can be facilitated. As the surfactant, those described in the above can be used.

1-2-2-2. Enclosure Step 2B2

Referring to FIG. 3-1 to FIG. 3-3B-H, enclosure step 2B2 will be described. In the step, the hydrophobic solvent 5 is introduced so as to laminate on the layer of the sample solution 4.

Although a method for introducing the hydrophobic solvent 5 is not particularly limited, the hydrophobic solvent 5 can be introduced, for example, from the opening of the open well into the region 21. At this time, the hydrophobic solvent 5 is preferably introduced so as to form a layer of the hydrophobic solvent 5 on the layer of the sample solution 4, as shown in FIG. 3-1B.

As the hydrophobic solvent 5, a solvent having a larger specific gravity than that of the sample solution 4 is used. The hydrophobic solvent 5 is preferably amphiphilic to the sample solution 4 sufficiently to replace their layers with each other but required to be not compatible with each other. If the amphiphilic property between the sample solution 4 and the hydrophobic solvent 5 is extremely low, replacement between the layer of the sample solution 4 and the layer of the hydrophobic solvent 5 does not occur. If the sample solution 4 and the hydrophobic solvent 5 are compatible with each other, the layer of the sample solution 4 and the layer of the hydrophobic solvent 5 are not discretely formed and do not form a laminate structure. Examples of such a hydrophobic solvent include those mentioned above. "Table 1" lists examples of the hydrophobic solvent 5 and their specific gravities.

The hydrophobic solvent 5 may contain a surfactant similarly to the sample solution 4 in order to facilitate layer replacement.

TABLE 1

| Second solvent | Density |
| --- | --- |
| PF-5052 | 1.700 g/mL at 25° C. |
| Fluorinert FC-72 | 1.680 g/mL at 25° C. |
| Fluorinert FC-770 | 1.790 g/mL at 25° C. |
| Fluorinert FC-3283 | 1.830 g/mL at 25° C. |
| Fluorinert FC-40 | 1.870 g/mL at 25° C. |
| Fluorinert FC-43 | 1.880 g/mL at 25° C. |
| Chloroform | 1.492 g/mL at 25° C. (lit.) |
| ASAHIKLIN AE-3000 | 1.470 g/mL at 25° C. |
| Novec 7000 | 1.400 g/mL |
| Novec 7100 | 1.520 g/mL |
| Novec 7200 | 1.430 g/mL |
| Novec 7300 | 1.660 g/mL |
| Krytox GPL-100 | 1.87 g/mL at 0° C. |
| Krytox GPL-101 | 1.89 g/mL at 0° C. |
| Krytox GPL-102 | 1.91 g/mL at 0° C. |
| Krytox GPL-103 | 1.92 g/mL at 0° C. |
| Krytox GPL-104 | 1.93 g/mL at 0° C. |
| Krytox GPL-105 | 1.94 g/mL at 0° C. |
| Krytox GPL-106 | 1.95 g/mL at 0° C. |
| Krytox GPL-107 | 1.95 g/mL at 0° C. |

The hydrophobic solvent 5 introduced onto the sample solution 4 and laminated on the sample solution 4 has a larger specific gravity than the sample solution 4. Because of this, the solvent 5 moves below the sample solution 4. More specifically, the layer of the sample solution 4 and the layer of the hydrophobic solvent 5 are replaced. The state (see, FIG. 3-1B) where the upper layer consists of the hydrophobic solvent 5 and the lower layer consists of the sample solution 4 changes to the state (see, FIG. 3-3H) where the upper layer consists of the sample solution 4 and the lower layer consists of the hydrophobic solvent 5. The process of layer replacement is schematically shown in FIG. 3-1C to FIG. 3-3G. During the process of the layer replacement, probe 1, probe 2 and the influenza virus particle or bacterial cell 3 are accommodated in each of the accommodation sites 214 such that they are pushed into the sites by the hydrophobic solvent 5 moving below the sample solution 4 (see, FIG. 3-2D to F). As a result, in the accommodation sites 214, droplets of the sample solution 4 containing probe 1, probe 2 and the influenza virus particle or bacterial cell 3 and coated with the hydrophobic solvent 5, are formed.

The volume of the droplets (virtually equal to the volume of the accommodation site 214) may be extremely small, for example, 10 aL to 100 nL, and preferably 1 fL to 1 pL.

In droplets of the sample solution 4 extremely small in volume, the reactions between a neuraminidase of the influenza virus particle or a bacterial cell with probe 1 and probe 2 proceed.

1-2-2-3. Detection Step 2B3

In the step, signals from probe 1 and probe 2 generated in droplets of the sample solution 4 are detected.

As described above, if influenza virus particles or bacterial cells are diluted to a sufficiently low concentration in the sample solution 4, since the number of influenza virus particles or bacterial cells 3 introduced in a single accommodation site 214 becomes 0 or at most 1, a droplet containing either one of an influenza virus particle and a bacterial cell is formed in the accommodation site 214.

In the case where a signal generated from probe 1 is detected and a signal generated from probe 2 is not detected in each droplet, an influenza virus can be detected in the droplet. In contrast, in the case where a signal generated from probe 1 and a signal generated from probe 2 are detected, the presence of a bacterial cell in the droplet (no influenza virus particle) can be detected.

Using the ratio of the number of the accommodation sites 214 where an influenza virus was detected and the number of the accommodation sites 214 where no influenza virus was detected and based on a standard curve (previously prepared) defining the relationship between the ratio and the number of virus particles, the amount of an influenza virus can be quantitatively determined (digital quantification).

2. Detection Kit of Influenza Virus and Diagnostic Kit of Influenza Infection

A detection kit of an influenza virus according to the present invention is a kit for detecting an influenza virus in a biological sample, which is isolated from a subject infected or suspected of being infected with an influenza virus. The detection kit of an influenza virus according to the present invention is used for diagnosing that a subject is with or without influenza infection. The detection kit of an influenza virus according to the present invention contains probe 1 and probe 2 as mentioned above. In addition to the probes, optionally a hydrophobic solvent as mentioned above, and the array 101 or the array 201, may be contained. These components of the kit can be sold as a group or singly.

Probe 1, probe 2 and the hydrophobic solvent are the same as defined above. With respect to the array 101 and the array 201, structures thereof will be more specifically described below.

The array 101 and the array 201 can be prepared by application of a common technique for forming microchips or arrays, such as photolithography, etching and lamination of substrates.

[Array 101]

As the material for the upper-layer portion 121, for example, glass, silicon and a polymer resin may be used.

The thickness of the upper-layer portion 121 is not particularly limited.

The lower surface of the upper-layer portion 121 (the surface facing the space 131) is preferably hydrophobic. The term "hydrophobic" is used in the same meaning as "lipophilic" and means that affinity for a hydrophobic solvent is higher than that for a hydrophilic solvent.

In the lower-layer portion 111, the accommodation sites 114 are mutually separated by the division wall 113 formed on a plate-like member 112. The bottom surface of the accommodation sites 114 may be the surface of the plate-like member 112.

As the material for the plate-like member 112, for example, glass, silicon or a polymer resin may be used.

The thickness of the plate-like member 112 is not particularly limited.

The division wall 113 can be formed by a resin layer formed on the surface of the plate-like member 112 and can be formed by, e.g., etching a water repellent resin or a fluorine-based polymer resin. As the fluorine-based polymer resin, for example, an amorphous fluororesin is mentioned. The amorphous fluororesin is preferably used because it has a high hydrophobicity and low toxicity to a biological sample.

As the amorphous fluororesin, at least one selected from CYTOP (R), TEFLON (R) AF2400 and TEFLON (R) AF1600, can be suitably used. Of them, CYTOP (R) is the most preferable since microfabrication is easy.

The shape of the accommodation sites 114 is not particularly limited and, for example, a cylindrical shape and a prism shape may be used.

The size of the accommodation sites 114 is not particularly limited as long as it can accommodate an influenza virus particle and/or a bacterial cell. The width (length in the horizontal direction) and the height (length in the vertical direction) (the height of the division wall 113) each fall within the range of, for example, 100 nm-100 μm, 200 nm-90 μm, 300 nm-80 μm, 400 nm-70 μm, 500 nm-60 μm, 600 nm-50 μm, 700 nm-40 μm, 800 nm-30 μm, 900 nm-20 μm, 1000 nm-10 μm, 2 μm-9 μm or 3 μm-8 μm.

As the accommodation sites 114, for example, 1,000,000 sites or more, may be highly densely arranged. Even if the sites are highly densely arranged, droplets of the sample solution 4 containing probe 1, probe 2 and the influenza virus particle or bacterial cell 3 and coated with the hydrophobic solvent 5 can be efficiently formed in individual accommodation sites 114, in accordance with the enclosure step described above.

The upper surface (surface facing the upper-layer portion 121) of the division walls 113 is preferably hydrophobic, whereas the surface of the plate-like member 112 forming the bottom surface of the accommodation sites 114 is preferably hydrophilic. The term "hydrophilic" means that the affinity for a hydrophilic solvent is higher than affinity for a hydrophobic solvent.

Since the bottom surface of the accommodation sites 114 is hydrophilic and the upper surface of division walls 113 and the lower surface of the upper-layer portion 121 are hydrophobic, the sample solution 4 can be smoothly introduced into the accommodation sites 114 in the introduction step 2A1. In addition, since the bottom surface of the accommodation sites 114 is hydrophilic and the upper surface of the division wall 113 is hydrophobic, the hydrophobic solvent 5 can be prevented from getting in the accommodation sites 114 in the enclosure step 2A2.

It is satisfactory that as long as the upper surface of the division walls 113 is hydrophobic, the side surface of the walls (the surface facing the accommodation sites 114) may be hydrophobic or hydrophilic.

The distance (the height of the space 131) between the lower surface of the upper-layer portion 121 (the surface facing the space 131) and the upper surface of the division wall 113 (the surface facing the upper-layer portion 121) can be reduced to the extent that the liquid can flow in the space 131 by the capillary phenomenon. The height of the space 131 falls within the range of, for example, 0.1 μm-5 mm, 0.5 μm-4 mm, 1 μm-3 mm, 2 μm-2 mm, 5 μm-1 mm, 10 μm-500 μm, 20 μm-400 μm, 30 μm-300 μm, 40 μm-200 μm or 50 μm-100 μm. If the height is less than 0.1 μm, the pressure required for feeding a liquid through the space 131 may be possibly too high.

[Array 201]

The lower-layer portion 211 of the array 201 may have the same constitution as the lower-layer portion 111 of the array 101. The plate-like member 212 and the division wall 213 constituting the lower-layer portion 211 may have the same constitution as the plate-like member 112 and the division wall 113 of the array 101.

Also, the accommodation sites 214 may have the same constitution as the accommodation sites 114 of the array 101.

The side wall 221 is formed of the same material as the plate-like member 212 and may be a surface of a member formed of, for example, glass, silicon, a polymer resin.

The height of the side wall 221 may be arbitrarily determined but the height is required to be more than the total thickness of a laminate of the layer of the sample solution 4 and the layer of the hydrophobic solvent 5.

Since the bottom surface of the accommodation site 214 is hydrophilic and the upper surface of the division wall 213 is hydrophobic, the hydrophobic solvent 5 can be prevented from getting in the accommodation site 214 in the enclosure step 2B2.

EXAMPLES

Now, the present invention will be described by way of Examples but the present invention is not limited to the examples.

Synthesis Example 1: Synthesis of HMRef-S-Neu5Ac

Compound 3 was synthesized in accordance with the steps shown in the following reaction scheme. Subsequently, HMRef-S-Neu5Ac was synthesized using compound 3.

[Formula 6]

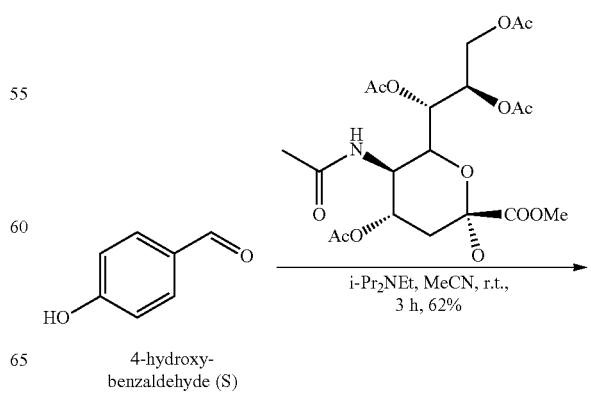

4-hydroxy-benzaldehyde (S)

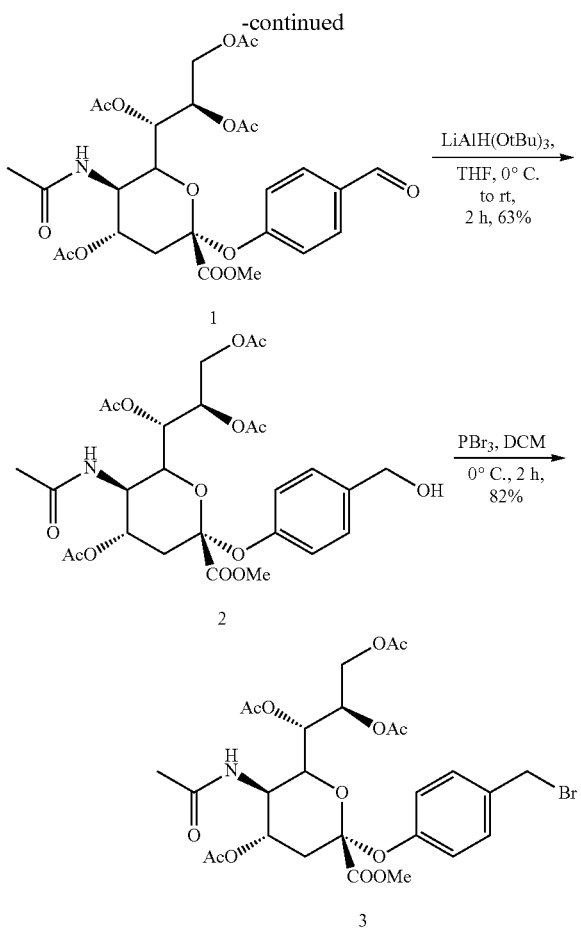

[Starting Material]

All chemistry substances used in synthesis were purchased from Tokyo Kasei Kogyo Co., Ltd., Wako Pure Chemical Industries Ltd. and Sigma Aldrich and used without additional purification.

[Measuring Apparatus]

NMR spectra were obtained by Bruker NMR AVANCE III 400 spectrometer [1H (400 MHz), 13C (101 MHz)] using a deuterated solvent.

High resolution ESI mass spectra were obtained by microOTOF II (Bruker).

HPLC purification was carried out by a JASCO PU-2087 Plus pump (GL Science Co., Ltd.) equipped with an Inertstil-ODS-3 column (φ10×250 mm (semi-sorting) and φ20×250 mm (sorting)) and UVIDEC-100-V detector (JASCO).

The solvent used in HPLC is obtained from Wako. Silica gel column chromatography was carried out using silica gel 60N (spherical, neutral, 63 to 210 μm; manufactured by Kanto Chemical Co., Inc.).

TLC was carried out by a silica gel plate F254 (0.25 mm (analysis); Merck, AKG).

UV-vis spectra were obtained by a Shimadzu UV-2450 spectrophotometer.

(1) Synthesis of Compound 1

To a solution of 4-hydroxybenzaldehyde (S, 479 mg, 3.9 mmol) and diisopropylethylamine (5 mL), an MeCN solution of N-acetyl-2-chloro-2-deoizunoylamine acid methyl ester 4,7,8,9-tetra acetate 3 (0.5 mL, 3.1 mmol) was added. The reaction mixture was stirred at room temperature for 3 hours. Thereafter, all solvents were removed and the residue was diluted with toluene (×3). The resultant residue was purified by silica gel chromatography (EtOAc:DCM, 1:1 to EtOAc) to obtain compound 1 as white foam (145 mg, 62%).

$^1$H NMR (400 MHz, CDCl$_3$) δ 1.93 (s, 3H, NHOAc), 2.05 (s, 3H, OAc), 2.06 (s, 3H, OAc), 2.12 (s, 3H, OAc), 2.19 (s, 3H, OAc), 2.30 (t, 1H, $^3J_{HH}$=12.5 Hz, H3$_{ax}$), 2.74 (dd, 1H, $^3J_{HH}$=13, 4.7 Hz, H3$_{eq}$), 3.65 (s, 3H, COOMe), 4.11 (m, 1H, H9), 4.13 (m, 1H, H5), 4.25 (dd, 1H, $^3J_{HH}$=12.4, 2.4 Hz, H9'), 4.60 (dd, 1H, $^3J_{HH}$=10.8, 1.6 Hz, H6), 4.98 (td, 1H, $^3J_{HH}$=10.4, 4.6, 1.8 HZ, H4), 5.23 (d, 1H, $^3J_{HH}$=10 Hz, H7), 5.35 (m, 1H, NH), 5.37 (m, 1H, H8), 7.18 (d, 2H, $^3J_{HH}$=8.7 Hz, Ar), 7.83 (d, 2H, $^3J_{HH}$=8.8 Hz, Ar), 9.93 (s, 1H, CHO). $^{13}$C NMR (101 MHz, CDCl$_3$) δ 20.7, 20.7, 20.8, 21.0, 23.2, 38.7, 49.5, 53.2, 62.0, 67.1, 68.4, 68.7, 73.6, 99.5, 118.9, 131.7, 132.0, 158.9, 168.2, 169.9, 170.1, 170.2, 170.6, 170.9, 190.9. HRMS (ESI$^+$): calcd for [M+Na$^+$] 618.17933, found 618.18094 (−1.6 mDa) for C$_{27}$H$_{34}$NaNO$_{14}$.

(2) Synthesis of Compound 2

Compound 1 (247 mg, 0.42 mmol) was dissolved in dry THF (5 mL) and LiAlH (OtBu)$_3$ (0.83 mL of 1.0 M THF solution) was added thereto at 0° C. The mixture was stirred at 0° C. for one hour. To the mixture, saturated NH$_4$Cl (aq) (5 mL) and EtOAc (10 mL) were added. The resultant mixture was stirred at room temperature for further one hour. To this mixture, an aqueous saturated solution of Rochelle salt (10 mL) was added. After a crude product was extracted with CHCl$_3$ (×3), the organic layer was removed under reduced pressure. Subsequently, the residue was purified by silica gel chromatography (MeOH:DCM 1:99 to 5:95) to obtain compound 2 as white foam (156 mg, 63%).

$^1$H NMR (400 MHz, CDCl$_3$) δ 1.90 (s, 3H, NHOAc), 2.04 (s, 3H, OAc), 2.04 (s, 3H, OAc), 2.12 (s, 3H, OAc), 2.13 (s, 3H, OAc), 2.21 (t, 1H, $^3J_{HH}$=12.6 Hz, H3$_{ax}$), 2.72 (dd, 1H, $^3J_{HH}$=12.9, 4.6 Hz, H3$_{eq}$), 3.68 (s, 3H, COOMe), 4.10 (m, 1H, H5), 4.14 (d, 1H, $^3J_{HH}$=5 Hz, H9), 4.28 (dd, 1H, $^3J_{HH}$=12.6, 2.6 Hz, H9'), 4.38 (dd, 1H, $^3J_{HH}$=10.8, 1.6 Hz, H6), 4.63 (s, 2H, CH$_2$OH), 4.95 (td, 1H, $^3J_{HH}$=10.4, 4.6, 1.8 HZ, H4), 5.27 (m, 1H, NH), 5.35 (m, 2H, H7, H8), 7.03 (d, 2H, $^3J_{HH}$=8.6 Hz, Ar), 7.27 (d, 2H, $^3J_{HH}$=8.6 Hz, Ar). $^{13}$C NMR (101 MHz, CDCl$_3$) δ 20.7, 20.8, 20.8, 21.0, 23.2, 38.2, 49.5, 52.9, 62.1, 64.9, 67.4, 68.8, 69.4, 73.4, 99.9, 120.3, 128.3, 136.7, 153.1, 168.1, 170.0, 170.1, 170.3, 170.7, 170.9. HRMS (ESI$^+$): calcd for [M+Na$^+$] 620.19498, found 620.19672 (−1.7 mDa) C$_{27}$H$_{36}$NaNO$_{14}$.

(3) Synthesis of Compound 3

Compound 2 (150 mg, 0.25 mmol) was dissolved in DCM (3 mL) and phosphorus tribromide (12 μL, 0.13 mmol) was added to the solution at 0° C. After stirring at 0° C. for 2 hours, the solution was washed with a saturated NaHCO$_3$ aqueous solution (×3) and a saturated saline solution (×1). The organic layer was dried over sodium sulfate and removed under reduced pressure to obtain compound 3 as white foam (136 mg, 82%).

$^1$H NMR (400 MHz, CDCl$_3$) δ 1.84 (s, 3H, NHOAc), 1.97 (s, 3H, OAc), 1.98 (s, 3H, OAc), 2.05 (s, 3H, OAc), 2.09 (s, 3H, OAc), 2.15 (t, 1H, $^3J_{HH}$=12.6 Hz, H3$_{ax}$), 2.63 (dd, 1H, $^3J_{HH}$=13, 4.7 Hz, H3eq), 3.58 (s, 3H, COOMe), 4.03 (m, 1H, H9), 4.10 (m, 1H, H5), 4.23 (m, 1H, H9'), 4.37 (m, 1H, H6), 4.40 (s, 2H, CH$_2$Br), 4.89 (td, 1H, $^3J_{HH}$=10.4, 4.6, 1.8 Hz, H4), 5.29 (m, 3H, H7, H8, NH), 6.95 (d, 2H, $^3J_{HH}$=8.7 Hz, Ar), 7.23 (d, 2H, $^3J_{HH}$=8.7 Hz, Ar). $^{13}$C NMR (101 MHz, CDCl$_3$) δ 19.7, 19.8, 19.8, 20, 22.2, 32.3, 37.2, 48.4, 52.0, 70.0, 66.3, 67.7, 68.1, 72.4, 98.8, 118.7, 129.2, 132.1, 152.8, 167.1, 169.0, 169.1, 169.2, 169.4, 169.6, 169.9. HRMS (ESI$^+$): calcd for [M+Na$^+$] 682.11057, found 682.10666 (3.9 mDa) C$_{27}$H$_{34}$BrNNaO$_{13}$.

(4) Synthesis of HMRef-S-Neu5Ac

In accordance with the following reaction scheme, HMRef-S-Neu5Ac was synthesized.

[Formula 7]

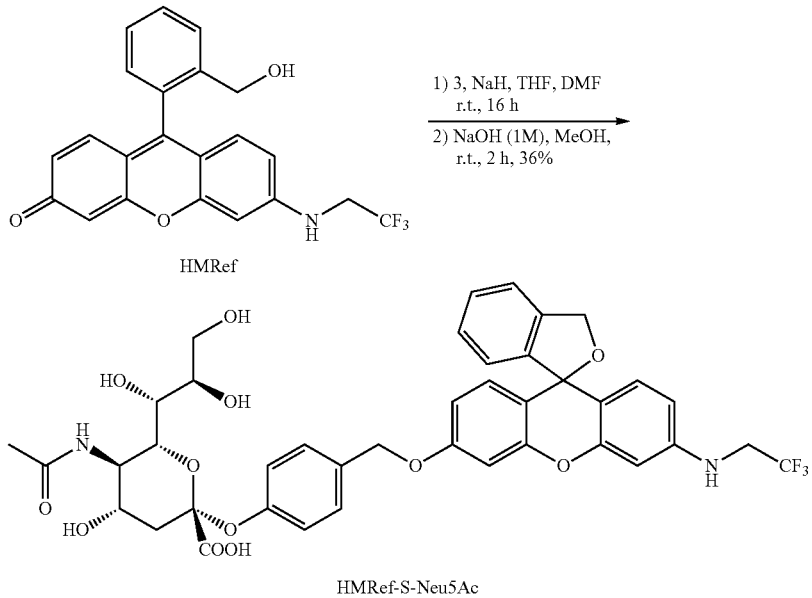

To HMRef (79 mg, 0.2 mmol) and NaH (6 mg, 0.26 mmol), dry THF (3 mL) and dry DMF (1 mL) were added. The mixture was stirred at 0° C. under an argon atmosphere. A dry THF (3 mL) solution of compound 3 (130 mg, 0.2 mmol) was added and the reaction mixture were stirred at room temperature for 16 hours. Thereafter, EtOAc (20 mL) was added. The mixture was washed with a saturated $NH_4Cl$ solution (×2) and a saturated saline solution (×1).

The organic layer was dried over sodium sulfate and distilled away under reduced pressure. The residue was dissolved in MeOH (6 mL). To this, 1M NaOH (aqueous solution) was added (3 mL). The resultant mixture was stirred at room temperature for 5 hours. Thereafter, the organic solvent was evaporated. The remaining aqueous solution was neutralized with 2M HCl and then lyophilized. Then, the residue was dissolved in a solution of MeOH: DCM, 1:4 and filtered to remove insoluble salts. The resultant solution was subjected to distillation under reduced pressure and the residue was purified by HPLC (Solution A: 100 mM TEAA buffer solution, Solution B: $CH_3CN$ 99%, $H_2O$ 1%. A/B=90/10 for 5 minutes, thereafter, 10/90 (gradient) for 15 minutes, then 10/90 for 15 minutes) and lyophilized to obtain an orange powder (36% by 2 steps).

$^1$H NMR (400 MHz, $CD_3OD$) δ 1.04 (t, 26H, TEAA), 1.84 (1H, t, $^3J_{HH}$=11.9 Hz, H3$_{ax}$), 1.90 (s, 3H, TEAA), 2.02 (s, 3H, $NHCOCH_3$), 2.55 (q, 17H, TEAA), 2.94 (dd, 1H, $^3J_{HH}$=12.2, 4.0 Hz, H3$_{eq}$), 3.54 (dd, 1H, $^3J_{HH}$=9.0, 1.6 Hz, H7), 3.66 (dd, 1H, $^3J_{HH}$=11.3, 5.4 Hz, H9), 3.74 (m, 1H, H5), 3.77 (m, 1H, H4), 3.81 (m, 1H, H9'), 3.85 (m, 2H, $NHCH_2CF_3$), 3.86 (m, 1H, H8), 3.91 (m, 1H, H6), 5.01 (s, 2H, $ArCH_2O$), 5.23 (s, 2H, $ArCH_2O$), 6.45 (dd, 1H, $^3J_{HH}$=8.6, $^4J_{HH}$=2.4 Hz, Ar), 6.50 (d, 1H, $^4J_{HH}$=2.3 Hz, Ar), 6.65 (dd, 1H, $^3J_{HH}$=8.7, $^4J_{HH}$=2.6 Hz, Ar), 6.67 (1H, $^3J_{HH}$=8.6, Ar), 6.78 (m, 1H, Ar), 6.79 (m, 1H, Ar), 6.82 (m, 1H, Ar), 7.24 (d, 2H, $^3J_{HH}$=8.7 Hz, Ar), 7.30 (m, 1H, Ar), 7.31 (d, 2H, $^3J_{HH}$=8.7 Hz, Ar), 7.39 (m, 1H, Ar), 7.43 (m, 1H, Ar). $^{13}$C NMR (101 MHz, $CD_3OD$) δ 11.2 (TEAA) 22.9, 24.4 (TEAA), 43.1, 45.8, 46.9 (TEAA), 54.3, 64.0, 69.3, 70.2, 72.6, 72.7, 73.1, 75.3, 85.5, 99.3, 104.0, 104.1, 109.7, 110.8, 114.7, 117.8, 118.1, 120.8, 121.9, 124.7, 124.8, 126.9 (q, $CF_3$), 129.3, 129.4, 130.2, 130.2, 130.9, 140.3, 146.0, 150.3, 152.1, 153.0, 157.0, 173.6, 175.6, 180.7 (TEAA) HRMS (ESI$^+$) L calcd for $[M+Na]^+$ 797.75163; found 797.75043 (−1.2 mDa).

HPLC analysis was carried out using linear gradient (0 min, 20% $CH_3CN$/0.1% TFAaq. To 15 min, 100% $CH_3CN$ 0.1% TFA aq; flow rate=1.0 mL/min). Fluorescence at 520 nm was checked.

Experimental Example 1: Reactivity of HMRef-S-Neu5Ac with Bacterium-Derived Neuraminidase A change in fluorescence intensity with elapsed time of a reaction between HMRef-S-Neu5Ac obtained in Synthesis Example 1 and an enzyme, *Arthrobacter ureafaciens*-derived neuraminidase, was examined.

A probe (HMRef-S-Neu5Ac) was dissolved in dimethyl sulfoxide (DMSO, fluorescence measurement grade, Dojindo Laboratories) to obtain a stock solution. The stock solution was diluted with a buffer solution (100 mm NaOAc, 2 mM $CaCl_2$, pH7.4) such that a final concentration of the probe became 1 μM, to obtain a measurement solution.

A fluorescence spectrum of the measurement solution was obtained by Hitachi F-700, every one second (excitation wavelength 490 nm, emission wavelength 520 nm). Sixty seconds after initiation of measurement, 0.01 U of *Arthrobacter ureafaciens*-derived neuraminidase was added singly or in combination with an enzyme inhibitor. The temperature at the time of measurement was set at 37° C. and the concentration of the enzyme inhibitor (DANA) was set at 100 μM.

Figure 4:
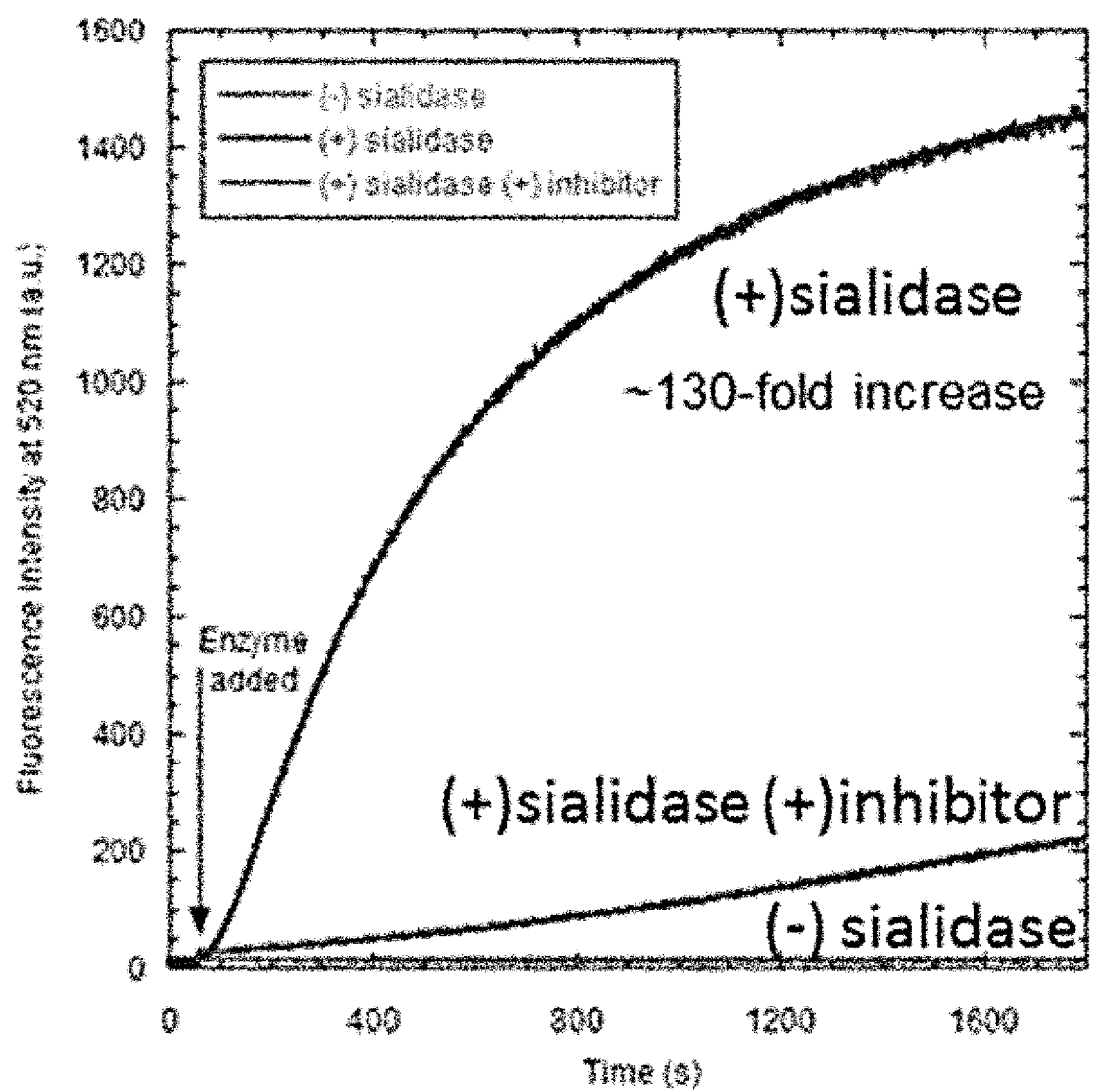
FIG. 4 is a graph showing a time-dependent change of fluorescence intensity observed in the enzymatic reaction of HMRef-S-Neu5Ac (Experimental Example 1) with neuraminidase derived from *Arthrobacter ureafaciens*.
Figure 5:
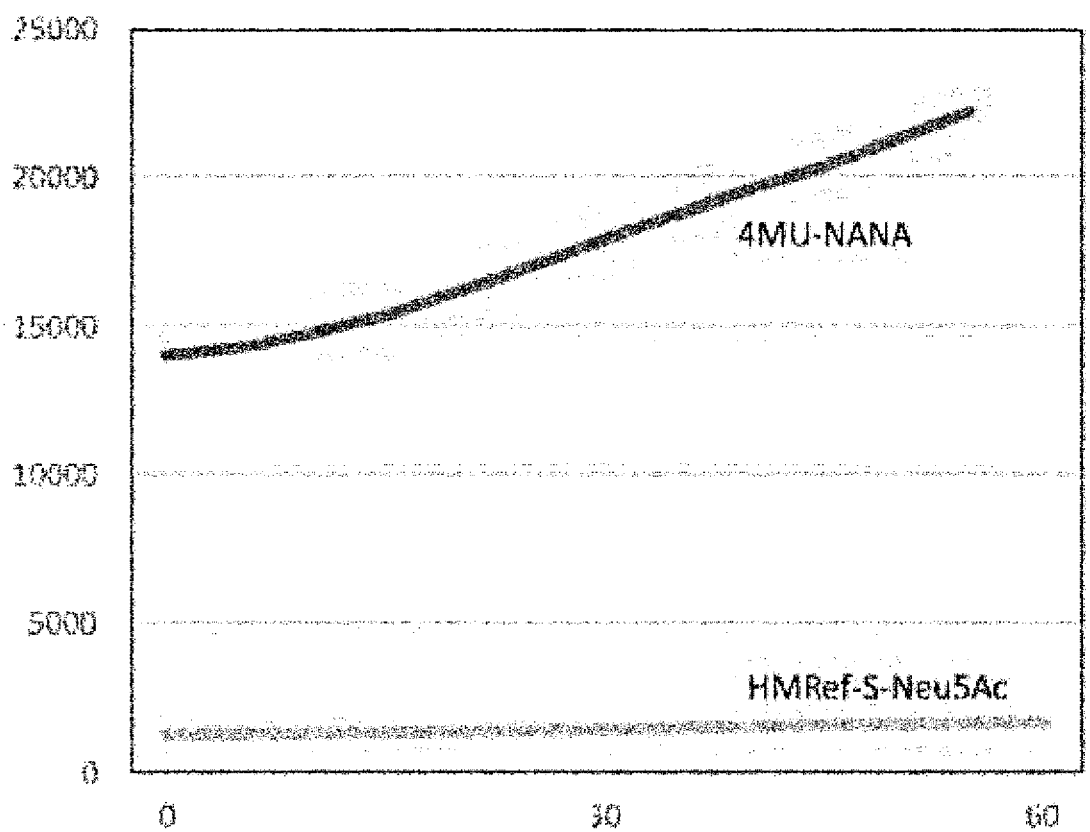
FIG. 5 is a graph showing time-dependent changes of fluorescence intensity observed in the enzymatic reactions of HMRef-S-Neu5Ac and 4MU-NANA (Experimental Example 2) with a neuraminidase derived from an influenza virus.
Figure 6:
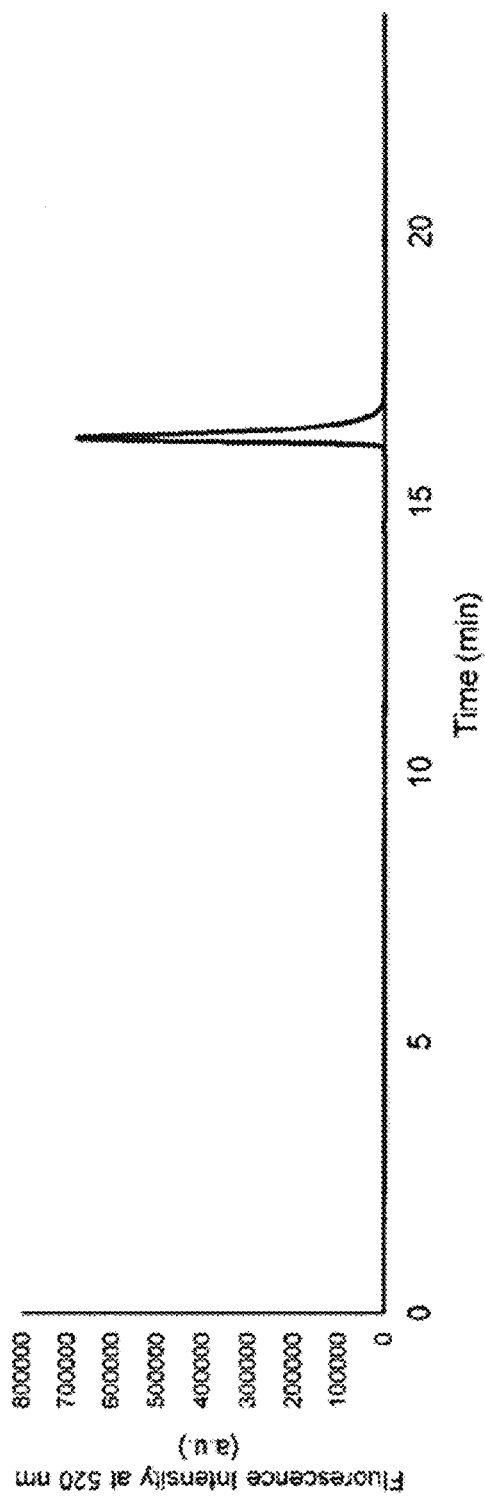
FIG. 6 is a graph showing HPLC analysis carried out using linear gradient (0 min, 20% CH3CN/0.1% TFAaq. To 15 min, 100% CH3CN 0.1% TFA aq; flow rate=1.0 mL/min). Fluorescence at 520 nm was checked.

The results are shown in FIG. 4. The fluorescence intensity of HMRef-S-Neu5Ac obtained by the reaction with the bacterium-derived neuraminidase, increased by 130 times.

When *Clostridium perfringens*-derived neuraminidase was used, the similar results were obtained. *Clostridium perfringens* is indigenous bacterium of humans and normally lives in the upper respiratory mucous membrane including the oral cavity.

Experimental Example 2: Reactivity of HMRef-S-Neu5Ac with Influenza Virus-Derived Neuraminidase A change in fluorescence intensity with elapsed time of a reaction between HMRef-S-Neu5Ac and an enzyme, influenza virus-derived neuraminidase, was examined in the same manner as in Experimental Example 1.

In the experimental example, a probe of 4MU-NANA (positive control) was used in addition to a probe of HMRef-S-Neu5Ac. As the final concentration of the probe of HMRef-S-Neu5Ac in the measurement solution was set at 100 μM, and that of the probe of 4MU-NANA was set at 1 mM.

To the measurement solutions, an influenza virus (A/PR8, strain II of the Institute of Medical Science) was added in a concentration of $5\times10^7$ PFU/mL and measurement for a fluorescence spectrum was initiated (excitation wavelength 360 nm, emission wavelength 448 nm). The temperature at the time of measurement was set at 25° C.

The results are shown in FIG. 5. The fluorescence intensity of the positive control, 4MU-NANA, increased over time, whereas no change in fluorescence intensity of HMRef-S-Neu5Ac was observed. From the results of Experimental Examples 1 and 2, it was found that HMRef-S-Neu5Ac reacts with the bacterium-derived neuraminidase but does not react with an influenza virus-derived neuraminidase.

REFERENCE SIGNS LIST

1: probe 1, 2: probe 2, 3: influenza virus particle or bacterial cell, 4: sample solution, 5: hydrophobic solvent, 101, 201: array, 111, 211: lower-layer portion, 112, 212: plate-like member, 113, 213: division wall, 114, 214: accommodation site, 121: upper-layer portion, 131: space, 21: region, 221: side wall

The invention claimed is:

1. A method for detecting an influenza virus in a biological sample, comprising:

(1) step 1 of mixing the biological sample with a first probe and a second probe, wherein the first probe is decomposed by an influenza virus-derived neuraminidase and a bacterium-derived neuraminidase to generate an optically detectable signal, the second probe is decomposed by the bacterium-derived neuraminidase to generate an optically detectable signal and not decomposed by the influenza virus-derived neuraminidase, and the signal generated from the first probe and the signal generated from the second probe can be optically discriminatorily detected, (2) step 2 of detecting signals generated from the first probe and the second probe, wherein if the ratio of an intensity of the signal generated from the first probe to an intensity of the signal generated from the second probe is equal to or more than a predetermined value, the presence of the influenza virus in the biological sample is detected, and if the ratio is less than the predetermined value, the absence of the influenza virus in the biological sample is detected.

2. The detection method according to claim 1, wherein the second probe is a compound represented by the following formula (1) or a salt thereof:

(1)

wherein $R_1$, if present, represents the same or different monovalent substituents present on a benzene ring, $R_2$ and $R_3$ each independently represent a hydrogen atom, an alkyl group having to 6 carbon atoms or a halogen atom, $R_4$ and $R_5$ each independently represent a hydrogen atom, an alkyl group having 1 to 6 carbon atoms or a halogen atom, $R_6$ represents a hydrogen atom, an alkyl group having 1 to 5 carbon atoms or an alkyl fluoride group having to 5 carbon atoms, $R_7$ and $R_8$, if present, each independently represent an alkyl group having 1 to 6 carbon atoms or an aryl group, wherein If X represents an oxygen atom, neither $R_7$ nor $R_8$ is present, $R_9$ is, independently at each occurrence, selected from a hydrogen atom, an alkyl group having 1 to 5 carbon atoms, an alkoxy group, a hydroxy group, a carboxyl group, a halogen atom, a sulfone group, an amino group, an alkoxycarbonyl group and an oxo groups, $R_{10}$, if present, represents the same or different monovalent substituents present on a benzene ring, X represents an oxygen atom, a silicon atom or a carbon atom, m represents an integer of 0 to 4,
n represents an integer of 1 to 3,
s represents an integer of 1, and
t represents an integer of 0 to 4.

3. The detection method according to claim 2, wherein the first probe is 2'-(4-methylumbelliferyl)-α-D-N-acetylneuraminic acid (4MU-NANA).

4. The detection method according to claim 1, based on a digital system.

5. A kit for detecting an influenza virus in a biological sample isolated from a subject infected or suspected of being infected with an influenza virus, comprising:
   a first probe that is decomposed by an influenza virus-derived neuraminidase and a bacterium-derived neuraminidase to generate an optically detectable signal, and
   a second probe that is decomposed by the bacterium-derived neuraminidase to generate an optically detectable signal and not decomposed by an influenza virus-derived neuraminidase, wherein
   the second probe is a compound represented by the following formula (1) or a salt thereof:

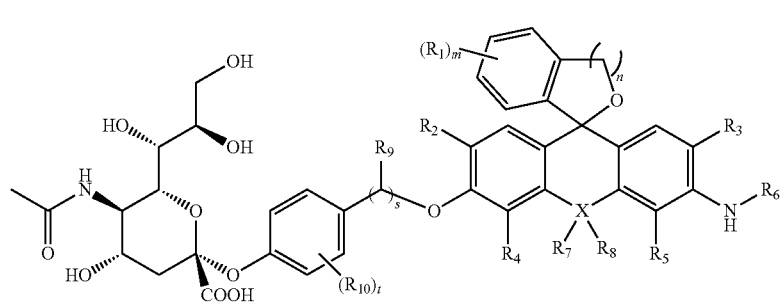

(1)

wherein
   $R_1$, if present, represents the same or different monovalent substituents present on a benzene ring,
   $R_2$ and $R_3$ each independently represent a hydrogen atom, an alkyl group having 1 to 6 carbon atoms or a halogen atom,
   $R_4$ and $R_5$ each independently represent a hydrogen atom, an alkyl group having 1 to 6 carbon atoms or a halogen atom,
   $R_6$ represents a hydrogen atom, an alkyl group having 1 to 5 carbon atoms or an alkyl fluoride group having 1 to 5 carbon atoms,
   $R_7$ and $R_8$, if present, each independently represent an alkyl group having 1 to 6 carbon atoms or an aryl group, wherein if X represents an oxygen atom, neither $R_7$ nor $R_8$ is present,
   $R_9$ is, independently at each occurrence, selected from a hydrogen atom, an alkyl group having 1 to 5 carbon atoms, an alkoxy group, a hydroxy group, a carboxyl group, a halogen atom, a sulfone group, an amino group, an alkoxycarbonyl group and an oxo group,
   $R_{10}$, if present, represents the same or different monovalent substituents present on a benzene ring,
   X represents an oxygen atom, a silicon atom or a carbon atom,
   m represents an integer of 0 to 4,
   n represents an integer of 1 to 3,
   s represents an integer of 1, and
   t represents an integer of 0 to 4.

6. The kit according to claim 5, wherein the first probe is 2'-(4-methylumbelliferyl)-α-D-N-acetylneuraminic acid (4MU-NANA).

7. A method for diagnosing whether a subject is infected or not with an influenza virus, comprising:
   (1) step 1 of mixing a biological sample, which is isolated from a subject infected or suspected of being infected with an influenza virus, a first probe and a second probe, wherein
   the first probe is decomposed by an influenza virus-derived neuraminidase and a bacterium-derived neuraminidase to generate an optically detectable signal,
   the second probe is decomposed by the bacterium-derived neuraminidase to generate an optically detectable signal and not decomposed by the influenza virus-derived neuraminidase, and
   the signal generated from the first probe and the signal generated from the second probe can be optically discriminatorily detected,
   (2) step 2 of detecting signals generated from the first probe and the second probe, wherein
   if the ratio of an intensity of the signal generated from the first probe to an intensity of the signal generated from the second probe is equal to or more than a predetermined value, it is determined that the subject is infected with an influenza virus, and
   if the ratio is less than the predetermined value, it is determined that the subject is not infected with an influenza virus.

* * * * *